United States Patent
Dietz et al.

(10) Patent No.: US 7,691,863 B2
(45) Date of Patent: Apr. 6, 2010

(54) PYRAZINE-2-CARBOXAMIDE DERIVATIVES AS CB2 RECEPTOR MODULATORS

(75) Inventors: Michel Dietz, Saint Louis (FR); Sabine Gruener, Grenzach-Wyhlen (DE); Paul Hebeisen, Basel (CH); Sylvie C. Meyer Reigner, Village-Neuf (FR); Matthias Nettekoven, Grenzach-Wyhlen (DE); Bernd Puellmann, Aesch BL (CH); Stephan Roever, Inzlingen (DE); Christoph Ullmer, Fischingen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/903,581

(22) Filed: Sep. 24, 2007

(65) Prior Publication Data

US 2008/0085905 A1    Apr. 10, 2008

(30) Foreign Application Priority Data

Oct. 4, 2006    (EP)    .................. 06121749

(51) Int. Cl.
*A61K 31/4965*    (2006.01)

(52) U.S. Cl. .................. 514/255.05; 544/106; 544/333; 544/405; 546/208; 546/268.1; 548/579

(58) Field of Classification Search ............ 514/255.05; 544/106, 333, 405; 546/208, 268.1; 548/579
See application file for complete search history.

(56) References Cited

U.S. PATENT DOCUMENTS

| 7,229,999 B2 | 6/2007 | Hebesien et al. |
| 2008/0070931 A1 | 3/2008 | Hebeisen et al. |

FOREIGN PATENT DOCUMENTS

| JP | 57038778 | * | 3/1982 |
| WO | WO 2004/018433 A1 | | 3/2004 |
| WO | WO 2004/029026 A1 | | 4/2004 |
| WO | WO 2004/083235 | * | 9/2004 |
| WO | WO 2004/111033 A1 | | 12/2004 |
| WO | WO 2005/016286 A2 | | 2/2005 |
| WO | WO 2005/075464 A1 | | 8/2005 |
| WO | WO 2007/147746 A1 | | 12/2007 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Patani, et al. Chem. Rev., 96, 1996, pp. 3147-3176.*
Hynes et al., Bioorganic & Medicinal Chemistry Letters, 12, pp. 2399-2402 (2002).
Smith et al., Eur. J. Pharmacology, 432, pp. 107-119 (2001).
Link et al., Eur. J. Med. Chem., 19, pp. 261-265 (1984).
Gaoni et al., J. Am. Chem. Soc., 86, pp. 1646-1647 (1964).
Mechoulam, R., (ed.) in "*Cannabinoids as Therapeutic Agents*", pp. 1-19 (1986) CRC Press.
Pertwee, R.G., Pharmaceut. Sci., 3, pp. 539-545 (1997).
Williamson et al., Drugs, 60, pp. 1303-1314 (2000).
U.S. Appl. No. 12/404,364, filed Mar. 16, 2009, Hebeisien et al., Not yet published pending patent application.
U.S. Appl. No. 12/404,365, filed Mar. 16, 2009, Hebeisien et al., Not yet published pending patent application.

* cited by examiner

*Primary Examiner*—James O Wilson
*Assistant Examiner*—Douglas M Willis
(74) *Attorney, Agent, or Firm*—George W. Johnston; Dennis P. Tramaloni; Brian C. Remy

(57) ABSTRACT

The present invention relates to compounds of the formula wherein $R^1$ to $R^4$ are as defined in the description and claims, and pharmaceutically acceptable salts thereof. The compounds are useful for the treatment and/or prophylaxis of diseases which are associated with the modulation of $CB_2$ receptors.

22 Claims, No Drawings

PYRAZINE-2-CARBOXAMIDE DERIVATIVES AS CB2 RECEPTOR MODULATORS

CROSS-REFERENCE TO RELATED APPLICATIONS

This application claims the benefit of European Patent Application No. 06121749.3, filed Oct. 4, 2006, which is hereby incorporated by reference in its entirety.

BACKGROUND OF THE INVENTION

The present invention relates to novel pyrazine-2-carboxamide derivatives, their manufacture, pharmaceutical compositions containing them and their use as medicaments. The active compounds of the present invention are useful in treating diseases associated with the modulation of $CB_2$ receptors.

Two different subtypes of cannabinoid receptors ($CB_1$ and $CB_2$) have been isolated and both belong to G protein coupled receptor superfamily. Alternative spliced forms of $CB_1$, $CB_{1A}$ and $CB_{1B}$ have also been described, but are expressed only at low levels in the tissues tested. (D. Shire, C. Carrillon, M. Kaghad, B. Calandra, M. Rinaldi-Carmona, G. Le Fur, D. Caput, P. Ferrara, J. Biol. Chem. 270 (8), 1995, 3726-31; E. Ryberg, H. K. Vu, N. Larsson, T. Groblewski, S. Hjorth, T. Elebring, S. Sjögren, P. J. Greasley, FEBS Lett. 579, 2005, 259-264). The $CB_1$ receptor is mainly located in the brain and to a lesser extent in several peripheral organs, whereas the $CB_2$ receptor is predominately distributed in the periphery primarily localized in spleen and cells of the immune system (S. Munro, K. L. Thomas, M. Abu-Shaar, Nature 365, 1993, 61-61). Therefore in order to avoid side effects a $CB_2$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *cannabis sativa* (marijuana), and has medicinal uses (R. Mechoulam (Ed.) in *"Cannabinoids as therapeutic Agents"*, 1986, pp. 1-20, CRC Press). $\Delta^9$-THC is a non-selective $CB_{1/2}$ receptor agonist and is available in the USA as dronabinol (Marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11), 1997, 539-545, E. M. Williamson, F. J. Evans, Drugs 60 (6), 2000, 1303-1314).

Following the cloning of $CB_1$- (1990) and $CB_2$-receptors (1993) two endocannabinoids (2-arachidonoylethanolamide (=anandamide) and 2-arachidonoylglycerol (2-AG)) were identified and further characterized. Subsequently, notable studies appeared showing anti-inflammatory properties of cannabinoids like $\Delta^9$-THC or metabolites of THC.

$CB_2$ receptor selective agonists/ligands are considered to be useful for the treatment of inflammatory disorders such as rheumatoid arthritis, asthma and chronic obstructive pulmonary disease while being devoid of psychotropic effects associated with $CB_1$ receptor agonism (J. Hynes, K. Leftheris, Bioorganic & Medicinal Chemistry Letters 12, 2002, 2399-2402). It is therefore an object of this invention to provide selective, directly acting $CB_2$ receptor agonists/ligands. Such agonists/ligands are useful in medical therapy, particularly in the treatment and/or prevention of diseases which are associated with the modulation of $CB_2$ receptors.

SUMMARY OF THE INVENTION

The present invention relates to the compounds of the formula I and all pharmaceutically acceptable salts thereof wherein formula I is:

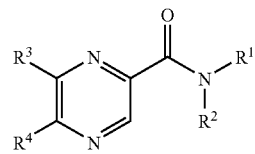

I wherein $R^1$-$R^{10}$ are as defined in the detailed description and in the claims. Compounds of formula I of the present invention are modulators of the $CB_2$ receptor and are useful in the treatment of diseases which are associated with the $CB_2$ receptor.

DETAILED DESCRIPTION OF THE INVENTION

Unless otherwise indicated, the following definitions are set forth to illustrate and define the meaning and scope of the various terms used to describe the invention herein.

In this specification the term "lower" used in combination with a named group means a group or substituent consisting of one to seven carbon atom(s). In preferred embodiments a "lower" group has one to four carbon atom(s).

The term "alkyl," alone or in combination with other groups, refers to a branched or straight-chain monovalent saturated aliphatic hydrocarbon radical of one to twenty carbon atoms. In preferred embodiments the alkyl has one to sixteen carbon atoms, and more preferably one to ten carbon atoms.

The term "lower alkyl" or "$C_{1-7}$-alkyl", alone or in combination with other groups, refers to a branched or straight-chain monovalent alkyl radical of one to seven carbon atoms. In preferred embodiments the alkyl has one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups are, for example, methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are, for example, —$CH_2$—O—$CH_3$, —$CH_2$—$CH_2$—O—$CH_3$, —$CH_2$—O—$CH_2$—$CH_3$ and the groups specifically exemplified herein. Most preferably, lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Preferred are $C_{3-7}$-hydroxyalkyl groups. Examples of lower hydroxyalkyl groups are 1-hydroxymethyl-3-methyl-butyl, 2-hydroxybutyl, 3-hydroxy-2,2-dimethylpropyl and the groups specifically exemplified herein.

The term "halogen" refers to fluorine, chlorine, bromine, or iodine. Preferred "halogen" groups are fluorine or chlorine.

The term "lower halogenalkyl" or "halogen-$C_{1-7}$-alkyl" refers to lower alkyl groups which are mono- or multiply substituted with halogen, preferably with fluoro or chloro, and most preferably with fluoro. Examples of lower halogenalkyl groups are —$CF_3$, —$CHF_2$, —$CH_2Cl$, —$CH_2CF_3$, —$CH(CF_3)_2$, —$CF_2$—$CF_3$ and the groups specifically exemplified herein. Especially preferred is 2,2,2-trifluoroethyl.

The term "cycloalkyl" or "$C_{3-7}$-cycloalkyl" refers to a monovalent carbocyclic radical of three to seven carbon atoms. In preferred embodiments the cycloakyl has three to five carbon atoms. This term is further exemplified by radicals such as cyclopropyl, cyclobutyl, cyclopentyl, cyclohexyl and cycloheptyl, with cyclopropyl, cyclobutyl and cyclopentyl being especially preferred.

The term "lower cycloalkylalkyl" or "$C_{3-7}$-cycloalkyl-$C_{1-7}$-alkyl" refers to a lower alkyl group as defined above which is mono- or multiply substituted with a cycloalkyl group as defined above. Examples of lower cycloalkylalkyl groups are —$CH_2$-cyclopropyl, —$CH_2$-cyclobutyl, —$CH_2$-cyclopentyl and the groups specifically exemplified herein.

The term "halogenphenyl" refers to a phenyl group that is substituted by one, two or three halogen groups as defined above. In preferred embodiments the "halogenphenyl" is a phenyl group that is substituted by one halogen group. Examples of lower halogenphenyl groups are 4-fluorophenyl, 4-chlorophenyl, 3-chlorophenyl and the groups specifically exemplified herein.

The term "heterocyclyl" in general refers to a saturated or partly unsaturated ring which can comprise one, two or three atoms selected from the group consisting of nitrogen, oxygen and sulphur. Examples of heterocyclyl rings include aziridinyl, azetidinyl, pyrrolidinyl, piperidinyl, tetrahydropyridyl, azepinyl, piperazinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, oxiranyl, oxetanyl, dihydropyranyl, tetrahydropyranyl and thiomorpholinyl. Preferred heterocyclyl groups are azetidinyl, pyrrolidinyl, piperidinyl, morpholinyl, thiomorpholinyl, azepanyl, tetrahydrofuryl and tetrahydropyranyl.

The term "lower heterocyclylalkyl" or "heterocyclyl-$C_{1-7}$-alkyl" refers to a lower alkyl group as defined above which is substituted with a heterocyclyl group as defined above. Preferred lower heterocyclylalkyl groups are —$CH_2$-tetrahydrofuryl, —$CH_2$-tetrahydropyranyl and the groups specifically exemplified herein.

The term "heteroaryl" refers to an aromatic 5- or 6-membered ring which can comprise one, two or three atoms selected from the group consisting of nitrogen, oxygen and sulphur. Examples of heteroaryl groups are, for example, furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, and pyrrolyl. The heteroaryl group can optionally be mono- or disubstituted independently by lower alkyl or halogen. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrimidinyl, imidazolyl, triazolyl, and thiazolyl, wherein said heteroaryl groups can optionally be mono- or disubstituted independently by lower alkyl or halogen. More preferred heteroaryl groups are pyridyl and pyrimidinyl and thiazolyl, wherein said heteroaryl groups can optionally be mono- or disubstituted independently by lower alkyl or halogen. Especially preferred are pyridine-2-yl and pyrimidin-2-yl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to the new compounds of formula I:

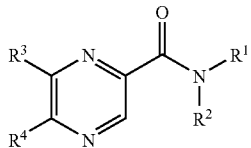

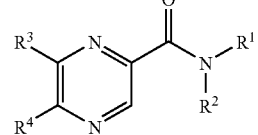

and all pharmaceutically acceptable salts thereof, wherein:
(a) $R^1$ is selected from the group consisting of:
  (1) lower alkyl,
  (2) lower hydroxyalkyl,
  (3) cycloalkyl, which is optionally substituted by a substituent selected from the group consisting of hydroxy, lower alkoxy and lower hydroxyalkyl,
  (4) lower cycloalkylalkyl,
  (5) lower heterocyclylalkyl,
  (6) —$CR^5R^6$—$COOR^7$; and
  (7) —$CR^5R^6$—$CONH_2$;
and $R^2$ is hydrogen; or alternatively, $R^1$ and $R^2$ together with the nitrogen atom to which they are attached form a 4-, 5-, 6- or 7-membered heterocyclic ring optionally containing a further heteroatom selected from the group consisting of nitrogen, oxygen and sulfur;
(b) one of $R^3$ and $R^4$ is —$OR^8$ or —$NR^9R^{10}$ and the other one of $R^3$ and $R^4$ is selected from the group consisting of:
  (1) lower alkylamino,
  (2) lower dialkylamino,
  (3) cycloalkylamino,
  (4) halogenphenyl, and
  (5) a heterocyclic ring selected from the group consisting of azetidinyl, pyrrolidinyl, piperidinyl, morpholinyl, thiomorpholinyl and azepanyl, wherein said heterocyclic ring is optionally substituted by halogen;
(c) $R^5$ is hydrogen or lower alkyl;
(d) $R^6$ is hydrogen or lower alkyl,
(e) $R^7$ is lower alkyl;
(f) $R^8$ is selected from the group consisting of:
  (1) lower alkyl,
  (2) lower halogenalkyl,
  (3) cycloalkyl,
  (4) lower cycloalkylalkyl,
  (5) lower phenylalkyl, wherein the phenyl is optionally substituted by a substituent selected from the group consisting of lower alkyl, lower alkoxy and halogen,
  (6) lower heterocyclylalkyl,
  (7) lower heteroarylalkyl,
  (8) lower alkoxyalkyl, and
  (9) lower hydroxyalkyl; and
(g) $R^9$ is lower alkyl, and $R^{10}$ is lower alkyl or lower alkoxyalkyl; or alternatively if one of $R^3$ or $R^4$ is halogenphenyl, then $R^9$ and $R^{10}$ together with the nitrogen atom to which they are attached may also form a heterocyclic ring selected from the group consisting of pyrrolidinyl and piperidinyl.

Preferably, the present invention relates to compounds of formula I having the formula and all pharmaceutically acceptable salts thereof, wherein:
(a) $R^1$ is selected from the group consisting of:
  (1) lower alkyl,
  (2) lower hydroxyalkyl,
  (3) cycloalkyl, which is optionally substituted by a substituent selected from the group consisting of hydroxy, lower alkoxy and lower hydroxyalkyl,
  (4) lower cycloalkylalkyl,
  (5) lower heterocyclylalkyl,
  (6) —$CR^5R^6$—$COOR^7$; and
  (7) —$CR^5R^6$—$CONH_2$;
and $R^2$ is hydrogen; or alternatively, $R^1$ and $R^2$ together with the nitrogen atom to which they are attached form a 4-, 5-, 6- or 7-membered heterocyclic ring optionally containing a further heteroatom selected from the group consisting of nitrogen, oxygen and sulfur;
(b) one of $R^3$ and $R^4$ is —$OR^8$ and the other one of $R^3$ and $R^4$ is selected from the group consisting of:
  (1) lower alkylamino,
  (2) lower dialkylamino,
  (3) cycloalkylamino, and
  (4) a heterocyclic ring selected from the group consisting of azetidinyl, pyrrolidinyl, piperidinyl, morpholinyl, thiomorpholinyl and azepanyl, wherein said heterocyclic ring is optionally substituted by halogen;
(c) $R^5$ is hydrogen or lower alkyl;
(d) $R^6$ is hydrogen or lower alkyl,
(e) $R^7$ is lower alkyl;
(f) $R^8$ is selected from the group consisting of:
  (1) lower alkyl,
  (2) lower halogenalkyl,
  (3) cycloalkyl,
  (4) lower cycloalkylalkyl,
  (5) lower phenylalkyl, wherein the phenyl is optionally substituted by a substituent selected from the group consisting of lower alkyl, lower alkoxy and halogen,
  (6) lower heterocyclylalkyl,
  (7) lower heteroarylalkyl,
  (8) lower alkoxyalkyl, and
  (9) lower hydroxyalkyl; and
(g) $R^9$ is lower alkyl, and $R^{10}$ is lower alkyl or lower alkoxyalkyl; or alternatively if one of $R^3$ or $R^4$ is halogenphenyl, then $R^9$ and $R^{10}$ together with the nitrogen atom to which they are attached may also form a heterocyclic ring selected from the group consisting of pyrrolidinyl and piperidinyl.

Preferred are compounds of formula I as defined above, wherein $R^1$ is selected from the group consisting of lower alkyl, lower hydroxyalkyl, lower heterocyclylalkyl, —$CR^5R^6$—$COOR^7$ and —$CR^5R^6$—$CONH_2$, $R^5$ and $R^6$ independently from each other are hydrogen or lower alkyl, $R^7$ is lower alkyl, and $R^2$ is hydrogen; or wherein $R^1$ and $R^2$ together with the nitrogen atom to which they are attached form a 4-, 5-, 6- or 7-membered heterocyclic ring optionally containing a further heteroatom selected from nitrogen, oxygen or sulfur.

Further preferred are those compounds of formula I, wherein $R^1$ is selected from the group consisting of lower alkyl, lower hydroxyalkyl, lower heterocyclylalkyl, —$CR^5R^6$—$COOR^7$ and —$CR^5R^6$—$CONH_2$, $R^5$ and $R^6$ independently from each other are hydrogen or lower alkyl, $R^7$ is lower alkyl, and $R^2$ is hydrogen.

Especially preferred are the compounds of formula I of the present invention, wherein $R^1$ is lower hydroxyalkyl or —$CR^5R^6$—$COOR^7$, $R^5$ and $R^6$ independently from each other are hydrogen or lower alkyl, $R^7$ is lower alkyl, and $R^2$ is hydrogen.

In specific embodiments, preferred are those compounds of formula I, wherein $R^1$ is lower hydroxyalkyl, and especially wherein $R^1$ is 1-hydroxymethyl-3-methylbutyl.

In specific embodiments, preferred are the compounds of formula I, wherein $R^1$ is —$CR^5R^6$—$COOR^7$, $R^5$ and $R^6$ independently from each other are lower alkyl, $R^7$ is lower alkyl, and $R^2$ is hydrogen, and especially wherein $R^1$ is 2-ethyl-butyric acid methyl ester.

Furthermore, compounds of formula I of the present invention are preferred, wherein $R^1$ and $R^2$ together with the nitrogen atom to which they are attached form a 4-, 5-, 6- or 7-membered heterocyclic ring optionally containing a further heteroatom selected from nitrogen, oxygen or sulfur.

Also preferred are compounds of formula I of the invention, wherein $R^1$ is cycloalkyl which is unsubstituted or substituted by a group selected from hydroxy, lower alkoxy and lower hydroxyalkyl.

Furthermore, compounds of formula I according to the present invention are preferred, wherein $R^4$ is selected from the group consisting of lower alkylamino, lower dialkylamino and cycloalkylamino or is a heterocyclic ring selected from azetidinyl, pyrrolidinyl, piperidinyl, morpholinyl, thiomorpholinyl and azepanyl, said heterocyclic ring being unsubstituted or substituted by halogen; and $R^3$ is —$OR^8$, wherein $R^8$ is selected from the group consisting of lower alkyl, lower halogenalkyl, cycloalkyl, lower cycloalkylalkyl, lower phenylalkyl, wherein the phenyl is unsubstituted or substituted by a group selected from lower alkyl, lower alkoxy and halogen, lower heterocyclylalkyl, lower heteroarylalkyl, lower alkoxyalkyl, and lower hydroxyalkyl. Another group of preferred compounds of formula I according to the invention are those, wherein $R^3$ is selected from the group consisting of lower alkylamino, lower dialkylamino and cycloalkylamino or is a heterocyclic ring selected from azetidinyl, pyrrolidinyl, piperidinyl, morpholinyl, thiomorpholinyl and azepanyl, said heterocyclic ring being unsubstituted or substituted by halogen; and $R^4$ is —$OR^8$, wherein $R^8$ is selected from the group consisting of lower alkyl, lower halogenalkyl, cycloalkyl, lower cycloalkylalkyl, lower phenylalkyl, wherein the phenyl is unsubstituted or substituted by a group selected from lower alkyl, lower alkoxy and halogen, lower heterocyclylalkyl, lower heteroarylalkyl, lower alkoxyalkyl, and lower hydroxyalkyl.

More preferably, compounds of formula I of the invention are those, wherein one of $R^3$ or $R^4$ is a heterocyclic ring selected from azetidinyl, pyrrolidinyl, piperidinyl, morpholinyl, thiomorpholinyl and azepanyl, said heterocyclic ring being unsubstituted or substituted by halogen.

Furthermore, compounds of formula I of the invention are preferred, wherein one of $R^3$ or $R^4$ is halogenphenyl. More preferably, compounds of formula I of the present invention are those, wherein $R^3$ is halogenphenyl, and especially wherein $R^3$ is selected from the group consisting of 4-fluorophenyl, 4-chlorophenyl and 3-chlorophenyl.

Further preferred are compounds of formula I according to the invention, wherein one of $R^3$ or $R^4$ is —$OR^8$, wherein $R^8$ is selected from the group consisting of lower alkyl, lower halogenalkyl, cycloalkyl, lower cycloalkylalkyl, lower phenylalkyl, wherein the phenyl is unsubstituted or substituted by a group selected from lower alkyl, lower alkoxy and halogen, lower heteroarylalkyl and lower alkoxyalkyl.

Furthermore, compounds of formula I of the invention are preferred, wherein one of $R^3$ or $R^4$ is —$OR^8$, wherein $R^8$ is selected from the group consisting of lower cycloalkylalkyl, lower phenylalkyl, wherein the phenyl is unsubstituted or substituted by a group selected from lower alkyl, lower alkoxy and halogen, and lower heteroarylalkyl, wherein the heteroaryl is pyridyl or pyrimidinyl.

Also preferred are compounds of formula I according to the invention, wherein one of $R^3$ or $R^4$ is —$OR^8$, wherein $R^8$ is lower halogenalkyl or lower alkoxyalkyl.

In specific embodiments, preferred are the compounds of formula I selected from the group consisting of:

6-cyclobutylmethoxy-5-pyrrolidin-1-yl-pyrazine-2-carboxylic acid (3-methyl-butyl)-amide, (6-cyclopentylmethoxy-5-pyrrolidin-1-yl-pyrazin-2-yl)-piperidin-1-yl-methanone, 6-cyclopropylmethoxy-5-pyrrolidin-1-yl-pyrazine-2-carboxylic acid cyclohexylamide, 6-cyclopropylmethoxy-5-pyrrolidin-1-yl-pyrazine-2-carboxylic acid ((S)-1-hydroxymethyl-3-methyl-butyl)-amide, 6-cyclopentylmethoxy-5-pyrrolidin-1-yl-pyrazine-2-carboxylic acid (3-methyl-butyl)-amide, 6-cyclopentylmethoxy-5-pyrrolidin-1-yl-pyrazine-2-carboxylic acid (tetrahydro-pyran-4-ylmethyl)-amide, 6-cyclopentylmethoxy-5-pyrrolidin-1-yl-pyrazine-2-carboxylic acid ((1R,2R)-2-hydroxy-cyclohexyl)-amide, 6-benzyloxy-5-pyrrolidin-1-yl-pyrazine-2-carboxylic acid ((S)-1-hydroxymethyl-3-methyl-butyl)-amide, 6-cyclopropylmethoxy-5-piperidin-1-yl-pyrazine-2-carboxylic acid ((S)-1-hydroxymethyl-3-methyl-butyl)-amide, 6-propoxy-5-pyrrolidin-1-yl-pyrazine-2-carboxylic acid ((S)-1-hydroxymethyl-3-methyl-butyl)-amide, 6-butoxy-5-pyrrolidin-1-yl-pyrazine-2-carboxylic acid ((S)-1-hydroxymethyl-3-methyl-butyl)-amide, 6-(4-fluoro-benzyloxy)-5-pyrrolidin-1-yl-pyrazine-2-carboxylic acid ((S)-1-hydroxymethyl-3-methyl-butyl)-amide, 6-(2-methoxy-ethoxy)-5-pyrrolidin-1-yl-pyrazine-2-carboxylic acid ((S)-1-hydroxymethyl-3-methyl-butyl)-amide, 2-ethyl-2-{[5-pyrrolidin-1-yl-6-(2,2,2-trifluoro-ethoxy)-pyrazine-2-carbonyl]-amino}-pentanoic acid methyl ester, (S)-2-[(6-cyclobutylmethoxy-5-pyrrolidin-1-yl-pyrazine-2-carbonyl)-amino]-propionic acid methyl ester, (R)-2-[(6-cyclobutylmethoxy-5-pyrrolidin-1-yl-pyrazine-2-carbonyl)-amino]-propionic acid methyl ester, 6-cyclobutylmethoxy-5-pyrrolidin-1-yl-pyrazine-2-carboxylic acid ((S)-1-hydroxymethyl-3-methyl-butyl)-amide, (S)-2-[(6-cyclopentylmethoxy-5-pyrrolidin-1-yl-pyrazine-2-carbonyl)-amino]-propionic acid methyl ester, (R)-2-[(6-cyclopentylmethoxy-5-pyrrolidin-1-yl-pyrazine-2-carbonyl)-amino]-propionic acid methyl ester, (S)-4-methyl-2-{[6-(pyridin-2-ylmethoxy)-5-pyrrolidin-1-yl-pyrazine-2-carbonyl]-amino}-pentanoic acid methyl ester, (S)-4-methyl-2-{[6-(pyrimidin-2-ylmethoxy)-5-pyrrolidin-1-yl-pyrazine-2-carbonyl]-amino}-pentanoic acid methyl ester, 2-ethyl-2-[(6-isopropoxy-5-piperidin-1-yl-pyrazine-2-carbonyl)-amino]-butyric acid methyl ester,
6-(2,2-dimethyl-propoxy)-5-piperidin-1-yl-pyrazine-2-carboxylic acid ((S)-1-hydroxymethyl-3-methyl-butyl)-amide,
6-(2-methoxy-ethoxy)-5-piperidin-1-yl-pyrazine-2-carboxylic acid ((S)-1-hydroxymethyl-3-methyl-butyl)-amide,
(S)-2-{[6-(2-methoxy-ethoxy)-5-piperidin-1-yl-pyrazine-2-carbonyl]-amino}-4-methyl-pentanoic acid methyl ester,
2-ethyl-2-{[5-morpholin-4-yl-6-(2,2,2-trifluoro-ethoxy)-pyrazine-2-carbonyl]-amino}-butyric acid methyl ester,
(S)-4-methyl-2-{[5-morpholin-4-yl-6-(2,2,2-trifluoro-ethoxy)-pyrazine-2-carbonyl]-amino}-pentanoic acid methyl ester,
6-(2,2-dimethyl-propoxy)-5-morpholin-4-yl-pyrazine-2-carboxylic acid ((S)-1-hydroxymethyl-3-methyl-butyl)-amide,
2-ethyl-2-{[6-(2-methoxy-ethoxy)-5-morpholin-4-yl-pyrazine-2-carbonyl]-amino}-butyric acid methyl ester,
2-{[5-cyclohexylamino-6-(2,2,2-trifluoro-ethoxy)-pyrazine-2-carbonyl]-amino}-2-ethyl-butyric acid methyl ester,
2-{[5-cyclohexylamino-6-(2,2-dimethyl-propoxy)-pyrazine-2-carbonyl]-amino}-2-ethyl-butyric acid methyl ester,
2-{[5-cyclohexylamino-6-(2-methoxy-ethoxy)-pyrazine-2-carbonyl]-amino}-2-ethyl-butyric acid methyl ester,
2-{[5-butylamino-6-(2,2,2-trifluoro-ethoxy)-pyrazine-2-carbonyl]-amino}-2-ethyl-butyric acid methyl ester,
2-{[5-butylamino-6-(2-methoxy-ethoxy)-pyrazine-2-carbonyl]-amino}-2-ethyl-butyric acid methyl ester,
2-[(5-diethylamino-6-isopropoxy-pyrazine-2-carbonyl)-amino]-2-ethyl-butyric acid methyl ester,
5-diethylamino-6-(2-methoxy-ethoxy)-pyrazine-2-carboxylic acid ((S)-1-hydroxymethyl-3-methyl-butyl)-amide,
(S)-2-{[5-diethylamino-6-(2-methoxy-ethoxy)-pyrazine-2-carbonyl]-amino}-4-methyl-pentanoic acid methyl ester,
5-diethylamino-6-(2-methoxy-ethoxy)-pyrazine-2-carboxylic acid ((S)-1-carbamoyl-3-methyl-butyl)-amide,
2-{[5-(4,4-difluoro-piperidin-1-yl)-6-(2,2-dimethyl-propoxy)-pyrazine-2-carbonyl]-amino}-2-ethyl-butyric acid methyl ester,
6-cyclopentylmethoxy-5-(4,4-difluoro-piperidin-1-yl)-pyrazine-2-carboxylic acid ((S)-1-hydroxymethyl-3-methyl-butyl)-amide,
(S)-2-{[6-cyclopentylmethoxy-5-(4,4-difluoro-piperidin-1-yl)-pyrazine-2-carbonyl]-amino}-4-methyl-pentanoic acid methyl ester,
2-{[5-(4,4-difluoro-piperidin-1-yl)-6-(2-methoxy-ethoxy)-pyrazine-2-carbonyl]-amino}-2-ethyl-butyric acid methyl ester,
2-ethyl-2-{[6-piperidin-1-yl-5-(2,2,2-trifluoro-ethoxy)-pyrazine-2-carbonyl]-amino}-butyric acid methyl ester,
5-cyclopropylmethoxy-6-piperidin-1-yl-pyrazine-2-carboxylic acid ((S)-1-hydroxymethyl-3-methyl-butyl)-amide,
6-[(2-methoxy-ethyl)-methyl-amino]-5-piperidin-1-yl-pyrazine-2-carboxylic acid ((S)-1-hydroxymethyl-3-methyl-butyl)-amide,
2-{[6-(4-fluoro-phenyl)-5-piperidin-1-yl-pyrazine-2-carbonyl]-amino}-2-methyl-propionic acid methyl ester,
2-{[6-(4-chloro-phenyl)-5-pyrrolidin-1-yl-pyrazine-2-carbonyl]-amino}-2-methyl-propionic acid methyl ester,
(R)-2-{[6-(4-chloro-phenyl)-5-(2,2,2-trifluoro-ethoxy)-pyrazine-2-carbonyl]-amino}-3-methyl-butyric acid methyl ester,
(R)-2-{[6-(3-chloro-phenyl)-5-(2,2,2-trifluoro-ethoxy)-pyrazine-2-carbonyl]-amino}-3-methyl-butyric acid methyl ester,
(R)-2-{[6-(3-chloro-phenyl)-5-cyclopropylmethoxy-pyrazine-2-carbonyl]-amino}-3-methyl-butyric acid methyl ester,
2-{[5-cyclopropylmethoxy-6-(4-fluoro-phenyl)-pyrazine-2-carbonyl]-amino}-2-methyl-propionic acid methyl ester,
2-{[6-(4-chloro-phenyl)-5-cyclopropylmethoxy-pyrazine-2-carbonyl]-amino}-2-methyl-propionic acid methyl ester, and any pharmaceutically acceptable salt thereof.

Especially preferred are the compounds selected from the group consisting of:
6-cyclopropylmethoxy-5-pyrrolidin-1-yl-pyrazine-2-carboxylic acid ((S)-1-hydroxymethyl-3-methyl-butyl)-amide,
6-cyclopropylmethoxy-5-piperidin-1-yl-pyrazine-2-carboxylic acid ((S)-1-hydroxymethyl-3-methyl-butyl)-amide,
6-(4-fluoro-benzyloxy)-5-pyrrolidin-1-yl-pyrazine-2-carboxylic acid ((S)-1-hydroxymethyl-3-methyl-butyl)-amide,
2-ethyl-2-{[5-pyrrolidin-1-yl-6-(2,2,2-trifluoro-ethoxy)-pyrazine-2-carbonyl]-amino}-pentanoic acid methyl ester,
6-cyclobutylmethoxy-5-pyrrolidin-1-yl-pyrazine-2-carboxylic acid ((S)-1-hydroxymethyl-3-methyl-butyl)-amide,
(R)-2-[(6-cyclopentylmethoxy-5-pyrrolidin-1-yl-pyrazine-2-carbonyl)-amino]-propionic acid methyl ester,
2-{[6-(4-chloro-phenyl)-5-cyclopropylmethoxy-pyrazine-2-carbonyl]-amino}-2-methyl-propionic acid methyl ester, and any pharmaceutically acceptable salt thereof.

The present invention also relates to a process for the manufacture of compounds of formula I as defined above, which process comprises coupling a compound of formula

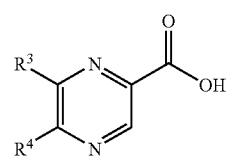

II wherein $R^3$ and $R^4$ are as defined herein before, with an amine of the formula

III wherein $R^1$ and $R^2$ are as defined herein before, with the help of an coupling agent under basic conditions, and, if desired, converting the resulting compound of formula I into a pharmaceutically acceptable salt thereof.

Coupling agents for the reaction of compounds of formula II with amines of formula III are for example (benzotriazol-1-yloxy)tripyrrolidino-phosphonium hexafluorophosphate (PyBOP), N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). Preferred coupling agent is PyBOP. Suitable bases include triethylamine and diisopropylethylamine (Huenig's base).

In more detail, the compounds of formula I can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

For example, compounds of formula I can be prepared according to scheme 1 starting from compound A by regioselective nucleophilic substitution of one bromo atom with a suitable nucleophile, in this case an alkoxide to give an intermediate AB. Advantageously such a reaction can be achieved by preparing the alkoxide in an inert solvent, for example THF in the presence of a base, for example sodium hydride and adding compound A to react typically at temperatures ranging from 0° C. to the boiling point of the solvent.

Compounds of the general formula AB can be transformed into compounds of the general formula AC by reaction with compounds of the general formula XA in which the abbreviation Lg stands for a suitable leaving group such as a halogen group or a mesylate group and Q stands for a carbon chain consisting of 2 to 3 methylene units or a chain consisting of a methylene unit, an oxygen atom and another methylene unit. Advantageously this reaction is run in the presence of a suitable base, for example sodium hydride, in an inert solvent, for example DMF, at temperatures from 0° C. to 80° C.

Transformation of a compound of the formula AC to a compound of formula AD can be effected by palladium catalyzed insertion of carbon monoxide into the aryl-bromine bond in a solvent containing an alcohol such as methanol under an atmosphere of carbon monoxide at pressures typically ranging from 1 bar to 200 bar and temperatures typically ranging from 20° C. to 150° C.

Saponification of compounds of the formula AD to compounds of the formula AE can be carried out in the presence of a suitable base such as a metal hydroxide, preferably sodium hydroxide, in an appropriate solvent such as tetrahydrofuran and mixtures thereof with water or methanol at temperatures ranging from 0° C. to 100° C., preferably at 20° C.

Coupling of compounds of the general formula AE with amines to give compounds of the general formula I can be carried out by methods used for the formation of peptide bonds. In one particular aspect of the invention compounds of the general formula AE are activated with a coupling reagent, for example PyBOP (benzotriazol-1-yloxy)tri-pyrrolidino-phosphonium hexafluorophosphate), and coupled to amines in an inert solvent such as DMF in the presence of suitable bases such as triethylamine or Huenig's base.

Compounds, wherein $R^3$ is a heterocyclic ring selected from azetidinyl, pyrrolidinyl, piperidinyl, morpholinyl, thiomorpholinyl and azepanyl, and $R^4$ is —$OR^8$, can be prepared in analog manner, however starting from a compound A':

The reaction sequence is not limited to the one displayed in scheme 1 but can alternatively be conducted according to the sequence shown in scheme 2.

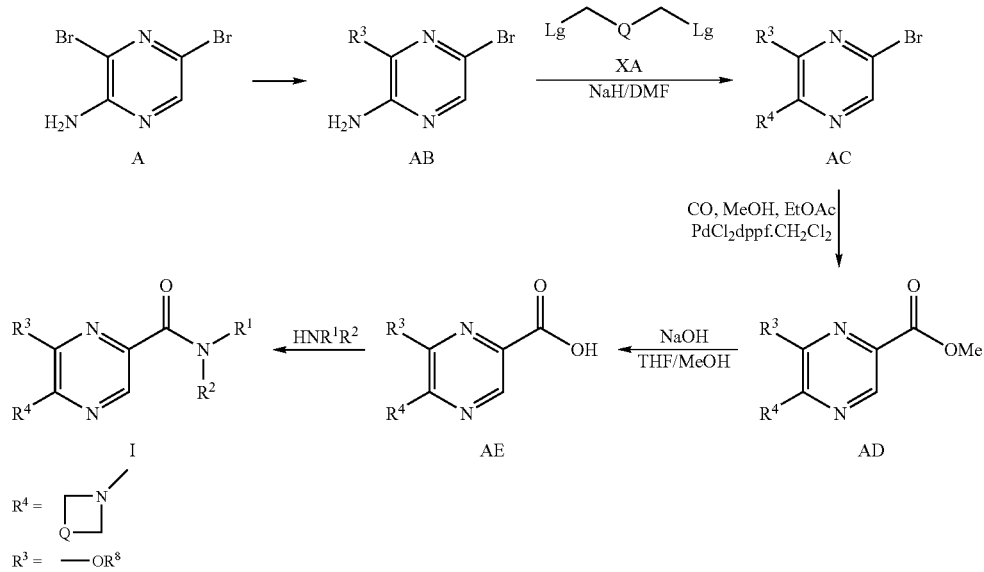

Scheme 2

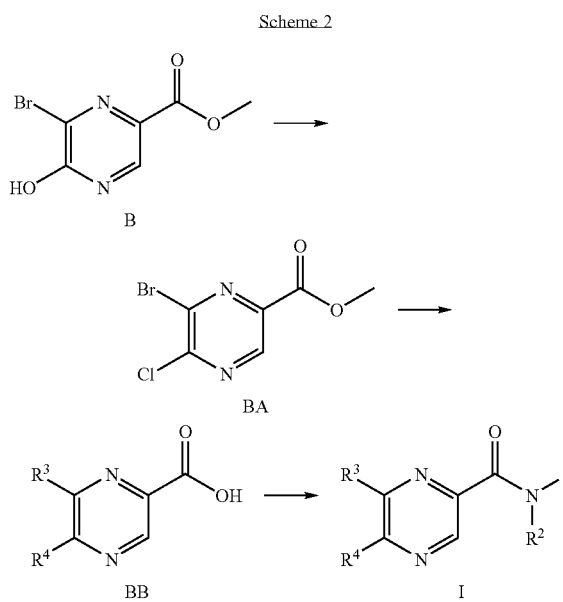

Compounds of formula I can be prepared according to scheme 2 starting from compound B which can be accessed from commercially available starting materials through bromination with $Br_2$ and a Lewis acid.

Chlorination of compound B with, for example $POCl_3$, gives access to compounds BA. In either a one pot reaction sequence or a sequence in which the particular reactions are performed separately compounds BB can be accessed by nucleophilic substitution of BA with alcohols followed by a nucleophilic substitution with amines concluded by a saponification with, for example KOH. Through reversion of the reagent addition isomeric pyrazines can be accessed.

Coupling of compounds of the general formula BB with amines to give compounds of the general formula I can be carried out by methods used for the formation of peptide bonds. In one particular aspect of the invention compounds of the general formula BB are activated with a coupling reagent, for example TBTU and coupled to amines in an inert solvent such as DMF in the presence of suitable bases such as triethylamine or Huenig's base.

Alternatively, the reaction sequence can be conducted according to the sequence shown in scheme 3.

Scheme 3

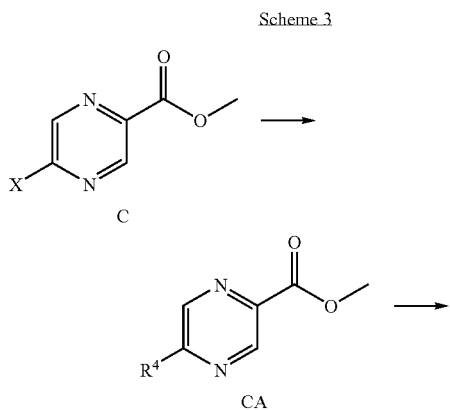

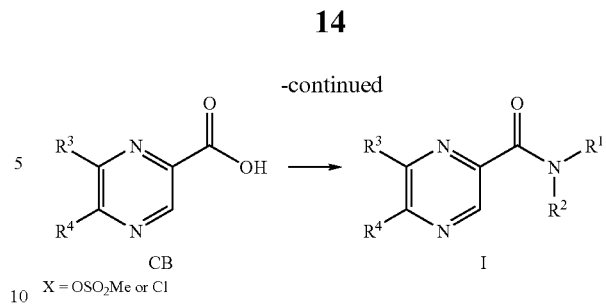

X = $OSO_2Me$ or Cl

Compounds of formula I can be prepared according to scheme 3 starting from compound C(X=$OSO_2Me$) which can be accessed from commercially available starting materials through mesylation with methane sulfonylchloride. The respective Chloro-pyrazine derivative C (X=Cl) is commercially available.

Nucleophilic substitution of compounds C with amines or alcohols gives access to compounds of formula CA.

In either a one pot reaction sequence or a sequence in which the particular reactions are performed separately compounds CB can be accessed by bromination of compounds CA followed by nucleophilic substitution with alcohols or amines and subsequently concluded by a saponification with, for example KOH.

Coupling of compounds of the general formula CB with amines to give compounds of the general formula I can be carried out by methods used for the formation of peptide bonds. In one particular aspect of the invention compounds of the general formula CB are activated with a coupling reagent, for example TBTU and coupled to amines in an inert solvent such as DMF in the presence of suitable bases such as triethylamine or Huenig's base.

Compounds of formula I, wherein $R^3$ or $R^4$ is a halogenphenyl residue can be prepared according to scheme 4 starting from compound A by reaction with aryl boronic acids to give an intermediate AB. Exemplified but by no means restricted to 4-fluorophenylboronic acid; 4-chlorophenylboronic acid or 3-chlorophenylboronic acid in an appropriate solvent such as 1,2-dimethoxyethane in the presence of a suitable catalyst such as tetrakis (triphenylphosphine) palladium (0) and a suitable base such as sodium carbonate at temperatures typically ranging from 0° C. to 120° C.; a protocol commonly known as the Suzuki reaction.

Transformation of a compound of the formula AB to a compound of formula DC can be effected by palladium catalyzed insertion of carbon monoxide into the aryl-bromine bond in a solvent containing an alcohol such as methanol under an atmosphere of carbon monoxide at pressures typically ranging from 1 bar to 200 bar and temperatures typically ranging from 20° C. to 150° C.

Compounds of the formula DC can be converted to compounds of the formula DD by reaction with a source of nitrite, preferably isoamyl nitrite in the presence of a source of bromide such as metal bromides or bromine containing solvents such as dibromomethane and an activating agent such as hydrobromic acid or trimethylbromosilane at temperatures ranging from −20° C. to 80° C., typically at ambient temperature.

Compounds of the general formula DD can be reacted with a wide variety of alcohols and amines in suitable solvents such as dimethylformamide or dimethylsulfoxide in the presence of a suitable base, preferably an excess of the amine itself or tertiary amine bases exemplified by triethylamine, Huenig's base or N,N,N',N'-tetramethylguanidine, in the case of reaction with amines or in case of reaction with alcohols, in presence of suitable bases such as metal hydrides, preferably sodium hydride or metal carbonates such as cesium carbonate to yield compounds of the general formula DE.

Saponification of compounds of the formula DE to compounds of the formula DF can be carried out in the presence of a suitable base such as a metal hydroxide, preferably lithium hydroxide, in an appropriate solvent such as tetrahydrofuran and mixtures thereof with water at temperatures ranging from 0° C. to 100° C., preferably at 20° C.

Coupling of compounds of the general formula DF with amines to give compounds of the general formula I can be carried out by methods used for the formation of peptide bonds. In one particular aspect of the invention compounds of the general formula DF are activated with oxalylchloride and coupled to amines in an inert solvent such as dichloromethane in the presence of suitable bases such as triethylamine or Huenig's base.

It will be appreciated, that the compounds of general formula I in this invention may be derivatised at functional groups to provide derivatives which are capable of conversion back to the parent compound in vivo.

As described above, the compounds of formula I or pharmaceutically acceptable salts thereof can be used as medicaments for the treatment and/or prophylaxis of diseases which are associated with the modulation of the $CB_2$ receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of $CB_2$ receptors.

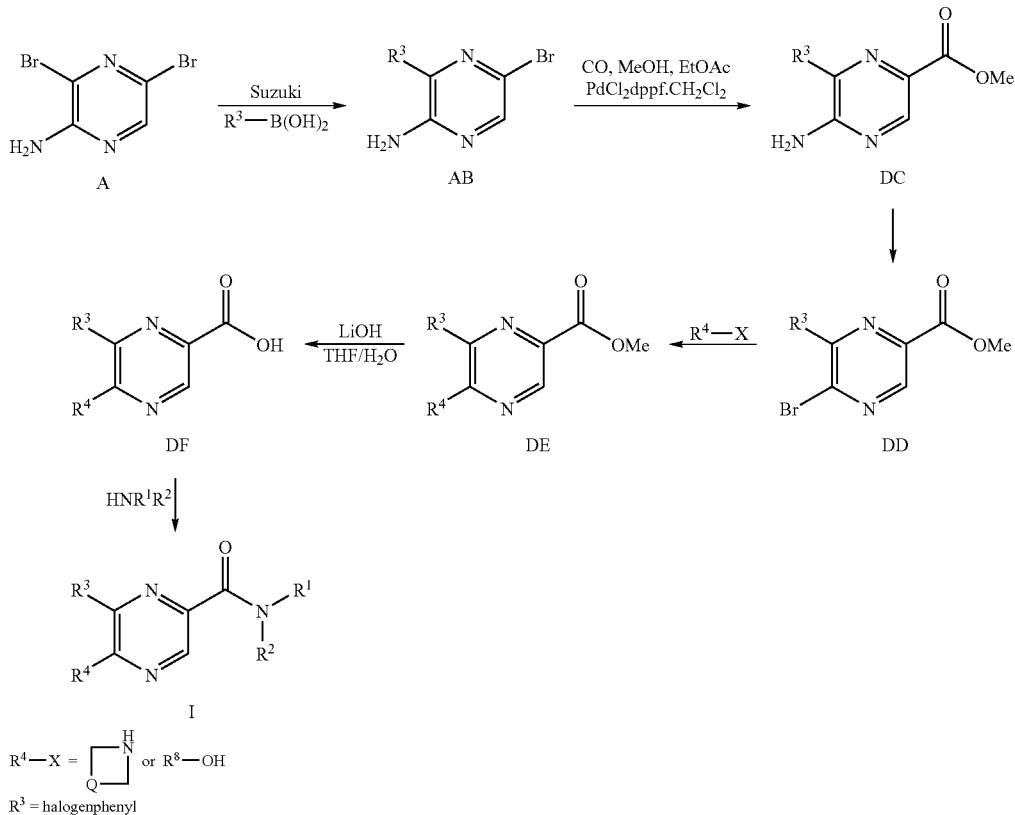

The invention further relates to compounds of formula I as defined above, when manufactured according to a process as defined above.

Some compounds of formula I may possess asymmetric centers and are therefore capable of existing in more than one stereoisomeric form. The invention thus also relates to compounds in substantially pure isomeric form at one or more asymmetric centers as well as mixtures, including racemic mixtures, thereof. Such isomers may be prepared by asymmetric synthesis, for example using chiral intermediates, or mixtures may be resolved by conventional methods, e.g., chromatography (chromatography with a chiral adsorbents or eluent), or use of a solving agent.

In another embodiment, the invention relates to a method for the treatment and/or prophylaxis of diseases which are associated with the modulation of $CB_2$ receptors, which method comprises administering a compound as defined above to a human being or animal.

The invention further relates to the use of compounds as defined above for the treatment and/or prophylaxis of diseases which are associated with the modulation of $CB_2$ receptors.

In addition, the invention relates to the use of compounds as defined above for the preparation of medicaments or pharmaceutical compositions for the treatment and/or prophylaxis of diseases which are associated with the modulation of $CB_2$ receptors. Such medicaments or pharmaceutical compositions comprise a compound as defined above.

In this context, the expression 'diseases associated with modulation of $CB_2$ receptors' means diseases which can be treated and/or prevented by modulation of $CB_2$ receptors. Such diseases encompass, but are not limited to, nausea, vomiting, multiple sclerosis, rheumatoid arthritis, allergy, asthma, alzheimer's disease, psoriasis, diarrhea, obesity, depression, huntington's disease, cardiovascular disorders, cerebrovascular disease, psychiatric disorders, inflammatory bowel disease, atherosclerosis, neuropathic pain, inflammatory pain, glaucoma, hepatitis, auto-immune disease, osteoporosis, pruritus, psoriasis, epilepsia, chronic obstructive pulmonary diseases (COPD), amyotrophic lateral sclerosis and hypertension. Modulators of the $CB_2$ receptor can be used as anxiolytics, analgetics, immunomodulators, oncolytic drugs, non-opioid analgesics, anti-psychotic drugs, anti-depressants, immunosuppressants and neurologic drugs or for the treatment of transplant rejection.

In a preferable aspect, the expression 'diseases associated with modulation of $CB_2$ receptors' relates to prevention and/or treatment of inflammation-related disorders such as arthritis, inflammatory bowel disease, allergy, atherosclerosis or cardiovascular disorders, with arthritis being especially preferred.

Demonstration of biological activities of the compounds of the present invention may be accomplished through in vitro, ex vivo, and in vivo assays that are well known in the art. For example, to demonstrate the efficacy of a pharmaceutical agent for the treatment of inflammation-related disorders such as arthritis, inflammatory bowel disease, allergy, or cardiovascular disease the following assays may be used.

In Vitro:

The following tests were carried out in order to determine the activity of the compounds of formula I:

The affinity of the compounds of the invention for cannabinoid $CB_2$ receptors was determined using membrane preparations of human embryonic kidney (HEK) cells in which the human cannabinoid $CB_2$ receptor is transiently transfected using the Semliki Forest virus system in conjunction with [3H]-CP-55,940 as radioligand. After incubation of a cell membrane preparation with the [3H]-ligand, with or without addition of compounds of the invention, separation of bound and free ligand was performed by filtration over glassfiber filters. Radioactivity on the filter was measured by liquid scintillation counting.

The affinity of the compounds of the invention for cannabinoid $CB_1$ receptors was determined using membrane preparations of human embryonic kidney (HEK) cells in which the human cannabinoid $CB_1$ receptor is transiently transfected using the Semliki Forest Virus system in conjunction with [3H]-CP-55,940 as radioligand. After incubation of a cell membrane preparation with the [3H]-ligand, with or without addition of compounds of the invention, separation of bound and free ligand was performed by filtration over glassfiber filters. Radioactivity on the filter was measured by liquid scintillation counting.

The cannabinoid $CB_2$ agonistic activity of compounds of the invention was determined by functional studies using CHO cells in which human cannabinoid $CB_2$ receptors are stably expressed. The stable expression of the human cannabinoid receptor in cell systems was first described by S. Munro, K. L. Thomas, M. Abu-Shaar, Nature 1993, 365, 61-65 ($CB_2$) respectively. Adenylyl cyclase was stimulated using forskolin and measured by quantifying the amount of accumulated cyclic AMP. Concomitant activation of $CB_2$ receptors by $CB_2$ receptor agonists can attenuate the forskolin-induced accumulation of cAMP in a concentration dependent manner.

The cannabinoid $CB_2$ receptor agonistic activity of compounds of formula I of the invention was also determined by a GTPγS binding assay using membrane preparations of HEK cells in which the human cannabinoid receptor $CB_2$ is transiently transfected using the Semliki Forest virus system in conjunction with [35S]-GTPγS. After incubation of the transfected cell membranes with [35S]-GTPγS, and GDP, with or without addition of compounds of the invention, separation of bound and free ligand was performed by filtration over glass-fiber filters. Radioactivity retained on the filter was measured by liquid scintillation counting.

The compounds of formula I show excellent affinity for the $CB_2$ receptor. The compounds of the present invention or their pharmaceutically acceptable salts are selective for the $CB_2$ receptor with affinities below $K_i$=0.5 μM, preferably below 200 nM, more preferably in the range 1 nM to 100 nM. They exhibit at least 10 fold selectivity against the $CB_1$ receptor.

| Compound of Example | $K_i$ [μM] $CB_2$ |
|---|---|
| 4 | 0.044 |
| 14 | 0.063 |
| 44 | 0.043 |

In Vivo:

Animals

Male NMRI or C57/Bl6 mice were used in this study and were obtained from Research Consulting Company Ltd (RCC) of Füllinsdorf (Switzerland). Mice, weighing 25-35 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

The in vivo activity of compounds of formula I of the invention was assessed for their ability to influence inflammation parameters in a model of acute peritonitis in animals. Cannabinoid receptor ligands are evaluated for their effects on the development of a peritoneal inflammation when elicited in mice treated with thioglycollate broth. $CB_2$ selective ligands should be able to suppress the peritoneal inflammation indicating an anti-inflammatory mechanism.

Intraperitoneal injection of thioglycollate induces an acute aseptic inflammation. As a consequence neutrophils, monocytes and lymphocytes transiently migrate into the peritoneal cavity. The number of differential white cell counts in the peritoneum can be quantitatively determined and used as a measure of the extent of the inflammatory reaction.

Short Description of the Model

Mice receive an intraperitoneal injection of 1 ml of 4% Brewers thioglycollate broth (Difco Laboratories, Detroit, Mich.). Four to 72 hours after the thioglycollate injection, mice were sacrificed and the peritoneal cavity is washed with PBS. After centrifugation and dilution, the lavage fluid is analyzed using an automated cell counting system to count the exact number of contributing neutrophils, monocytes and lymphocytes. Additionally the lavage fluid is analyzed for the content/change of inflammatory cytokines. $CB_2$ selective agents were shown to inhibit the migration of macrophages, the production of inflammatory cytokines (IL-12, TNFa) and to increase the production of anti-inflammatory IL-10 (S. R. Smith, G. Denhardt, C. Terminelli, European Journal of Pharmacology, 432 (2001) 107-119).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatin capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

The following are a list of abbreviations and/or acronyms with their corresponding definitions used in the following examples:

LC=HPLC chromatography on an Atlantis C18 reverse phase column using a water/acetonitrile mobile phase (0.1% formic acid) linked to a Waters Micromass® ZQTM mass spectrometer (Mobile phase: A=Formic acid (aq) 0.1%; B=Formic acid (acetonitrile) 0.1%; Flow rate 1 mL/min; Injection volume 3 mL; Detector 215 nm (nominal); Gradient Time/% organic Phase: 0 min/5%, 2.5 min/100%, 2.7 min/100%, 2.71 min/5%, 3.0 min/5%); Rt=retention time; MS=mass spectrometry; EI=electron impact; ISP=ion spray, corresponds to ES=electrospray; (M+H)=the molecular weight of the compound plus a proton; NMR data are reported in parts per million ($\delta$) relative to internal tetramethylsilane and are referenced to the deuterium lock signal from the sample solvent ($d_6$-DMSO unless otherwise stated); coupling constants (J) are in Hertz, mp=melting point; bp=boiling point; TBTU=O-(Benzotriazol-1-yl)-N,N',N'-tetramethyl-uronium-tetrafluoroborate; DMF=dimethylformamide, dppf=1,1'-bis(diphenylphosphino)ferrocene; PyBOP=Benzotriazol-1-yloxy)tripyrrolidino-phosphonium hexafluorophosphate.

Example 1

6-Cyclobutylmethoxy-5-pyrrolidin-1-yl-pyrazine-2-carboxylic acid (3-methyl-butyl)-amide a) 5-Bromo-3-cyclobutylmethoxy-pyrazin-2-ylamine Sodium hydride (0.96 g, 23.7 mmol) was added in portions to a solution of cyclobutanemethanol (2.2 mL, 23.7 mmol) in tetrahydrofuran (30 mL) at 0° C., the reaction mixture was stirred at room temperature for 45 minutes. A solution of 2-amino-3,5-dibromopyrazine (3.0 g, 11.9 mmol) in tetrahydrofuran (10 mL) was added and the reaction mixture was heated at 50° C. for 16 hours. The reaction mixture was cooled to room temperature and water (2 mL) was added, the whole was then concentrated in vacuo to give a brown oil. The crude product was purified by flash column chromatography (100% dichloromethane) to give 5-bromo-3-cyclobutyl-methoxy-pyrazin-2-ylamine as a pale yellow solid, 3.19 g (100% yield). LC@215 nm; Rt 2.11: 93%, m/z (ES$^+$): 259 (M+H).

b) 5-Bromo-3-cyclobutylmethoxy-2-pyrrolidin-1-yl-pyrazine

Sodium hydride (0.98 g, 25.6 mmol) was added in portions to a solution of 5-bromo-3-cyclobutylmethoxy-pyrazin-2-ylamine (3.1 g, 12.2 mmol) in N,N-dimethylformamide (60 mL) under nitrogen at room temperature. After 20 minutes 1-bromo-4-chlorobutane (1.5 mL, 13.4 mmol) was added and the reaction mixture was stirred for 16 hours. The reaction mixture was poured onto ice and the whole was extracted with ethyl acetate (50 mL) and washed with water (30 mL×2), the organic layer was dried over MgSO$_4$ and concentrated in vacuo. The crude product was purified by flash column chromatography (30% ethyl acetate/heptane) to afford 5-bromo-3-cyclobutylmethoxy-2-pyrrolidin-1-yl-pyrazine as a yellow solid 2.27 g (60% yield). LC@215 nm; Rt 2.72: 100%, m/z (ES$^+$): 313 (M+H).

c) 6-Cyclobutylmethoxy-5-pyrrolidin-1-yl-pyrazine-2-carboxylic acid methyl ester A 50 mL bomb with a glass liner was charged with the 5-bromo-3-cyclobutylmethoxy-2-pyrrolidin-1-yl-pyrazine (2.27 g, 7.3 mmol), ethyl acetate (6 mL, degassed), methanol (7 mL, degassed) and triethylamine (2.0 mL, 14.5 mmol). PdCl$_2$dppfCH$_2$Cl$_2$ (0.29 g, 0.36 mmol) was charged to the bomb; the bomb was sealed and degassed under vacuum. The reaction was purged with carbon monoxide (×5) then pressurized to 5 bar and heated to 100° C. for 1 hour. The reaction mixture was filtered through celite and washed with methanol then ethyl acetate and the filtrate was concentrated in vacuo. The residue was dissolved in ethyl acetate (100 mL) and washed with water (100 mL) the organic layer was dried over MgSO$_4$ and concentrated in vacuo to afford 6-cyclobutyl-methoxy-5-pyrrolidin-1-yl-pyrazine-2-carboxylic acid methyl ester as an orange solid, 2.2 g (75% yield). LC@215 nm; Rt 2.39: 75%, m/z (ES$^+$): 292 (M+H).

d) 6-Cyclobutylmethoxy-5-pyrrolidin-1-yl-pyrazine-2-carboxylic acid

Sodium hydroxide 2M (10 mL) was added to a solution of the 6-cyclobutylmethoxy-5-pyrrolidin-1-yl-pyrazine-2-carboxylic acid methyl ester (2.2 g, 7.4 mmol) in a (1:1) mixture of methanol and tetrahydrofuran (30 mL), the reaction mixture was stirred at room temperature for 2 hours. The reaction mixture was concentrated in vacuo and the residue was dissolved in ether (30 mL) and extracted with water (50 mL), the aqueous layer was washed with ether (2×50 mL) until only product remained in the aqueous layer. The aqueous layer was cooled to 0° C. and acidified with concentrated hydrochloric acid until precipitation was observed. The precipitate was filtered and dried in vacuo to afford 6-cyclobutylmethoxy-5-pyrrolidin-1-yl-pyrazine-2-carboxylic acid as a cream solid 1.65 g (80% yield) LC@215 nm; Rt 1.98: 93%, m/z (ES$^+$): 278 (M+H).

e) 6-Cyclobutylmethoxy-5-pyrrolidin-1-yl-pyrazine-2-carboxylic acid (3-methyl-butyl)-amide A solution of PyBOP (156.1 mg, 0.3 mmol) in N,N-dimethylformamide (0.5 mL) was added to a solution of the 6-cyclobutylmethoxy-5-pyrrolidin-1-yl-pyrazine-2-carboxylic acid (62.7 mg, 0.2 mmol) in N,N-dimethylformamide (1 mL) and the reaction mixture was left to stand for 20 minutes. 3-methyl butylamine (34.9 mg, 0.4 mmol) and N-ethyldiisopropylamine (103.4 mg, 0.8 mmol) were added and the reaction mixture was shaken for 16 hours. The solvent was removed in vacuo and the crude product was purified by preparative HPLC to afford 6-cyclobutylmethoxy-5-pyrrolidin-1-yl-pyrazine-2-carboxylic acid (3-methyl-butyl)-amide as a solid 35.8 mg (52% yield) LC@215 nm; Rt 2.63: 100%, m/z (ES$^+$): 347 (M+H).

Example 2

(6-Cyclopentylmethoxy-5-pyrrolidin-1-yl-pyrazin-2-yl)-piperidin-1-yl-methanone a) 5-Bromo-3-cyclopentylmethoxy-pyrazin-2-ylamine To a solution of 4.24 g (0.042 mol) cyclopentanmethanol in 40 mL DMSO was added 1.74 g sodium hydride 55% in oil and the mixture was stirred at room temperature for 45 min. To the resulting solution was added 5.06 g (0.020 mol) 2-amino-3,5-dibromopyrazine and the mixture was stirred at room temperature for 20 h. To the resulting solution was added 1.0 g (0.011 mol) cyclopentanemethanol and the mixture was stirred at room temperature for 20 h. The reaction mixture was partitioned between water and ethyl acetate. The phases were separated and the organic phase washed with water (3×) and brine, dried over magnesium sulfate, evaporated and the residue was purified by chromatography on silica gel with heptane:ethyl acetate=9:1 to 3:1 to yield 3.845 g of the title compound as yellow orange crystals melting at 78-79° C.

b) 5-Bromo-3-cyclopentylmethoxy-2-pyrrolidin-1-yl-pyrazine

To a solution of 0.544 g (0.0020 mol) 5-bromo-3-cyclopentylmethoxy-pyrazin-2-ylamine in 10 mL dimethylformamide was added 0.349 g (0.0080 mol) sodium hydride 55% in oil and the mixture was stirred at room temperature for 20 min. To the resulting suspension was added 0.345 mL (0.0030 mol) 1-bromo-2-chlorobutane and the mixture was stirred at room temperature for 2 h. The reaction mixture was partitioned between 10% aqueous citric acid and ethyl acetate. The phases were separated and the organic phase was washed with water and 10% aqueous sodium bicarbonate, dried over sodium sulfate, evaporated and the residue was purified by chromatography on silica gel with heptane:ethyl acetate=9:1 to yield 0.579 g (0.0018 mol) of the title compound as yellowish crystals melting at 54-55° C.

c) 6-Cyclopentylmethoxy-5-pyrrolidin-1-yl-pyrazine-2-carboxylic acid methyl ester To a solution of 0.563 g (0.0017 mol) 5-bromo-3-cyclopentylmethoxy-2-pyrrolidin-1-yl-pyrazine in 4 mL methanol and 2 mL ethyl acetate was added 0.050 g PdCl$_2$dppfCH$_2$Cl$_2$ and 0.48 mL (0.0035 mol) triethylamine and the mixture was stirred under an atmosphere of 70 bar carbon monoxide at 110° C. for 18 h in an autoclave. The solids were removed by filtration and the mother liquor was partitioned between water and ethyl acetate. The phases were separated and the organic phase was washed with water (2×) dried over sodium sulfate, evaporated and the residue was purified by chromatography on silica gel with dichloromethane:ethyl acetate=19:1 to yield 0.423 g of the title compound as slightly yellow orange crystals melting at 69-70° C.

d) 6-Cyclopentylmethoxy-5-pyrrolidin-1-yl-pyrazine-2-carboxylic acid

To a solution of 0.423 g (0.0014 mol) 6-cyclopentyl-methoxy-5-pyrrolidin-1-yl-pyrazine-2-carboxylic acid methyl ester in 5.5 mL tetrahydrofuran, 1.40 mL methanol and 1.4 mL water was added 2.8 mL of a 1M solution of lithium hydroxide in water and the mixture was stirred at room temperature for 4 h. The reaction mixture was partitioned between 10% aqueous citric acid and ethyl acetate. The phases were separated and the organic phase was washed with water (2×) and brine, dried over sodium sulfate and evaporated to yield 0.396 g (0.0014 mol) of the title compound as white crystals melting at 204-206° C.

e) (6-Cyclopentylmethoxy-5-pyrrolidin-1-yl-pyrazin-2-yl)-piperidin-1-yl-methanone To a solution of 0.0874 g (0.0003 mol) 6-cyclopentyl-methoxy-5-pyrrolidin-1-yl-pyrazine-2-carboxylic acid in 1.0 mL dichloromethane was added 0.047 g (0.00035 mol)(1-chloro-N,N,2-trimethyl-1-propenylamine and the mixture was stirred at room temperature for 45 min. To the resulting solution was added 0.0683 g (0.0008 mol) piperidine and the mixture was stirred at room temperature for 2 h. The reaction mixture was partitioned between 10% citric acid and dichloromethane. The phases were separated and the organic phase was washed with water and brine, dried over sodium sulfate, evaporated and the residue was purified by chromatography on silica gel with dichloromethane:ethyl acetate=1:1 to yield 0.064 g (0.00018 mol) of the title compound as beige crystals melting at 61-62° C.

Example 3

6-Cyclopropylmethoxy-5-pyrrolidin-1-yl-pyrazine-2-carboxylic acid cyclohexylamide The title compound was synthesized in analogy to Example 1, using 2-amino-3,5-dibromopyrazine, cyclopropylmethanol, 1-bromo-4-chlorobutane and aminocyclohexane as starting materials; yield 47.4 mg, 59%. LC@215 nm; Rt 2.46: 100%, m/z (ES$^+$): 345 (M+H).

Example 4

6-Cyclopropylmethoxy-5-pyrrolidin-1-yl-pyrazine-2-carboxylic acid ((S)-1-hydroxymethyl-3-methyl-butyl)-amide The title compound was synthesized in analogy to Example 1, using 2-amino-3,5-dibromopyrazine, cyclopropylmethanol, 1-bromo-4-chlorobutane and (S)-leucinol as starting materials; yield 44.4 mg, 53%. LC@215 nm; Rt 2.72: 100%, m/z (ES$^+$): 361 (M+H).

Example 5

6-Cyclopentylmethoxy-5-pyrrolidin-1-yl-pyrazine-2-carboxylic acid (3-methyl-butyl)-amide The title compound was synthesized in analogy to Example 1, using 2-amino-3,5-dibromopyrazine, cyclopentylmethanol, 1-bromo-4-chlorobutane and 3-methyl butylamine as starting materials; yield 51.8 mg, 57%. LC@215 nm; Rt 2.32: 100%, m/z (ES$^+$): 389 (M+H).

Example 6

6-Cyclopentylmethoxy-5-pyrrolidin-1-yl-pyrazine-2-carboxylic acid (tetrahydro-pyran-4-ylmethyl)-amide The title compound was synthesized in analogy to Example 1, using 2-amino-3,5-dibromopyrazine, cyclopentylmethanol, 1-bromo-4-chlorobutane and 4-aminomethyltetrahydropyran as starting materials; yield 47.6 mg, 57%. LC@215 nm; Rt 2.16: 100%, m/z (ES$^+$): 363 (M+H).

Example 7

6-Cyclopentylmethoxy-5-pyrrolidin-1-yl-pyrazine-2-carboxylic acid ((1R,2R)-2-hydroxy-cyclohexyl)-amide The title compound was synthesized in analogy to Example 1, using 2-amino-3,5-dibromopyrazine, cyclopentylmethanol, 1-bromo-4-chlorobutane and (1R,2R)-2-aminocyclohexanol as starting materials; yield 55.1 mg, 61%. LC@215 nm; Rt 2.31: 100%, m/z (ES$^+$): 389 (M+H).

Example 8

6-Benzyloxy-5-pyrrolidin-1-yl-pyrazine-2-carboxylic acid ((S)-1-hydroxymethyl-3-methyl-butyl)-amide The title compound was synthesized in analogy to Example 1, using 2-amino-3,5-dibromopyrazine, benzyl alcohol, 1-bromo-4-chlorobutane and (S)-leucinol as starting materials; yield 12.2 mg, 13%. LC@215 nm; Rt 2.27: 100%, m/z (ES$^+$): 399 (M+H).

Example 9

6-Cyclopropylmethoxy-5-piperidin-1-yl-pyrazine-2-carboxylic acid ((S)-1-hydroxymethyl-3-methyl-butyl)-amide a) 5-Methanesulfonyloxy-pyrazine-2-carboxylic acid methyl ester A mixture of 3.34 g (22 mmol) methyl 5-hydroxypyrazine-2-carboxylate (commercially available), 2.73 g (24 mmol) methane sulfonyl chloride and 3.29 g (33 mmol) NEt$_3$ in 40 mL DCM was stirred at room temperature for 4 h. Water and Na$_2$CO$_3$ was added and the organic layer was separated and dried with MgSO$_4$. Evaporation yielded 3.7 g (73%) of the title compound which was used without further purification. 300-MHz-$^1$H-NMR (DMSO): δ=9.06 (d, J=1.2 Hz, 1H, 3-H), 8.83 (d, J=1.2 Hz, 1H, 6-H), d=3.97 (s, 3H, OMe), 3.74 (s, 3H, SO$_2$Me).

b) 5-Piperidin-1-yl-pyrazine-2-carboxylic acid methyl ester

A mixture of 1 g (4.3 mmol) 5-methanesulfonyloxy-pyrazine-2-carboxylic acid methyl ester and 0.733 (8.6 mmol) piperidine was shaken at room temperature for 4 h. Subsequent purification on silica eluting with a gradient formed from DCM and methanol yielded after evaporation of the product fractions 0.625 g (66%) of the title compound as light yellow crystals. m/z (ES$^+$): 222.0 (M+H).

c) 6-Bromo-5-piperidin-1-yl-pyrazine-2-carboxylic acid methyl ester

A mixture of 0.625 g (2.8 mmol) 5-piperidin-1-yl-pyrazine-2-carboxylic acid methyl ester, 1.12 g (7 mmol) Br$_2$ and 0.142 g (0.48 mmol) FeBr$_3$ in 10 mL CHCl$_3$ was stirred at room temperature for 16 h. The mixture was treated with DCM and water and the organic layer separated and dried with MgSO$_4$. 0.12 g (14%) of the title compound was obtained after evaporation as light yellow crystals which were used without further purification. m/z (ES$^+$): 299.9 (M+H).

d) 6-Cyclopropylmethoxy-5-piperidin-1-yl-pyrazine-2-carboxylic acid

A mixture of 0.12 g (0.4 mmol) 6-bromo-5-piperidin-1-yl-pyrazine-2-carboxylic acid methyl ester, 0.029 g (0.4 mmol) cyclopropyl methanol and 0.018 g (0.41 mmol) NaH (55% suspension in oil) in 2 mL DMF was shaken for an extended period of time. Afterwards, 0.1 mL KOH (5N aq.) was added and the mixture was heated to 45° C. for 1 h. After addition of formic acid the mixture was subjected to purification by preparative HPLC on reversed phase eluting with a gradient formed from acetonitrile, water and formic acid. The combined product fractions were evaporated to yield 11 mg (10%) of the title compound. m/z (ES+): 278.1 (M+H).

e) 6-Cyclopropylmethoxy-5-piperidin-1-yl-pyrazine-2-carboxylic acid ((S)-1-hydroxymethyl-3-methyl-butyl)-amide A mixture of 11 mg (0.04 mmol) 6-cyclopropylmethoxy-5-piperidin-1-yl-pyrazine-2-carboxylic acid, 15.3 mg (0.048 mmol) TBTU, 15.3 mg (0.119 mmol) DIPEA and 7 mg (0.059 mmol) (S)-2-amino-4-methyl-pentan-1-ol (commercially available) in 1 mL DMF was shaken at room temperature for 16 h. The mixture was subjected to purification by preparative HPLC on reversed phase eluting with a gradient formed from acetonitrile, water and NEt$_3$. The combined product fractions were evaporated to yield 10.5 mg (70%) of the title compound. m/z (ES+): 377.5 (M+H).

Example 10

6-Propoxy-5-pyrrolidin-1-yl-pyrazine-2-carboxylic acid ((S)-1-hydroxymethyl-3-methyl-butyl)-amide a) 6-Bromo-5-hydroxy-pyrazine-2-carboxylic acid methyl ester A mixture of 2 g (13 mmol) methyl 5-hydroxypyrazine-2-carboxylate (commercially available), 0.192 g (0.65 mmol) FeBr$_3$, 0.7 mL (14 mmol) Br$_2$ in 20 mL CHCl$_3$ was refluxed for 16 h. After evaporation of all volatiles the residue was used without further purification in the consecutive step.

b) 6-Bromo-5-chloro-pyrazine-2-carboxylic acid methyl ester

A mixture of 6-bromo-5-hydroxy-pyrazine-2-carboxylic acid methyl ester and 9.75 mL (10.7 mmol) POCl$_3$ was refluxed for 3 h and subsequently quenched with 200 g ice. The mixture was extracted with DCM, the combined organic phases were dried with MgSO$_4$ and evaporated to dryness the residue was purified by column chromatography on silica eluting with a gradient formed from ethyl acetate and heptane. The product fractions were combined and evaporated to dryness to yield 0.95 g (29%) of the title compound as light yellow solid. 300-MHz-$^1$H-NMR (DMSO): δ=9.00 (s, 1H, 3-H), d=4.04 (s, 3H, OMe).

c) 6-Propoxy-5-pyrrolidin-1-yl-pyrazine-2-carboxylic acid

A mixture of 71.3 mg (0.28 mmol) 6-bromo-5-chloro-pyrazine-2-carboxylic acid methyl ester, 182.4 mg (0.56 mmol) Cs$_2$CO$_3$ and 17 mg (0.286 mmol) propanol in 1 mL DMF was heated to 60° C. for 16 h. Subsequently, 60 mg (0.84 mmol) pyrrolidine was added and the mixture was heated to 100° C. for 16 h. 0.2 mL water and 0.05 mL 5N KOH was added and heated to 60° C. for 2 h. The mixture was purified by preparative HPLC on reversed phase eluting with a gradient formed from acetonitrile, water and formic acid. The combined product fractions were evaporated to yield 12 mg (17%) of the title compound. m/z (ES+): 252.0 (M+H).

d) 6-Propoxy-5-pyrrolidin-1-yl-pyrazine-2-carboxylic acid ((S)-1-hydroxymethyl-3-methyl-butyl)-amide A mixture of 6 mg (0.024 mmol) 6-propoxy-5-pyrrolidin-1-yl-pyrazine-2-carboxylic acid, 9.3 mg (0.029 mmol) TBTU, 9.3 mg (0.072 mmol) DIPEA and 4.2 mg (0.036 mmol) (S)-2-amino-4-methyl-pentan-1-ol (commercially available) in 1 mL DMF was shaken at room temperature for 16 h. After addition of formic acid the mixture was subjected to purification by preparative HPLC on reversed phase eluting with a gradient formed from acetonitrile, water and formic acid. The combined product fractions were evaporated to yield 2 mg (24%) of the title compound. m/z (ES+): 351.5 (M+H).

Example 11

6-Butoxy-5-pyrrolidin-1-yl-pyrazine-2-carboxylic acid ((S)-1-hydroxymethyl-3-methyl-butyl)-amide a) 6-Butoxy-5-pyrrolidin-1-yl-pyrazine-2-carboxylic acid In analogy to the procedure described for the synthesis of 6-propoxy-5-pyrrolidin-1-yl-pyrazine-2-carboxylic acid (example 10, step c), the title compound was synthesized from 6-Bromo-5-chloro-pyrazine-2-carboxylic acid methyl ester, butanol (commercially available), pyrrolidine (commercially available) and subsequent saponification with KOH in 8% yield. m/z (ES+): 266.0 (M+H).

b) 6-Butoxy-5-pyrrolidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-butoxy-5-pyrrolidin-1-yl-pyrazine-2-carboxylic acid and (S)-2-amino-4-methyl-pentan-1-ol (commercially available). m/z (ES+): 365.5 (M+H).

Example 12

6-(4-Fluoro-benzyloxy)-5-pyrrolidin-1-yl-pyrazine-2-carboxylic acid ((S)-1-hydroxymethyl-3-methyl-butyl)-amide a) 6-(4-Fluoro-benzyloxy)-5-pyrrolidin-1-yl-pyrazine-2-carboxylic acid In analogy to the procedure described for the synthesis of 6-propoxy-5-pyrrolidin-1-yl-pyrazine-2-carboxylic acid (example 10, step c), the title compound was synthesized from 6-bromo-5-chloro-pyrazine-2-carboxylic acid methyl ester, (4-fluoro-phenyl)-methanol (commercially available), pyrrolidine (commercially available) and subsequent saponification with KOH in 13% yield. m/z (ES+): 318.0 (M+H).

b) 6-(4-Fluoro-benzyloxy)-5-pyrrolidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-(4-fluoro-benzyloxy)-5-pyrrolidin-1-yl-pyrazine-2-carboxylic acid and (S)-2-amino-4-methyl-pentan-1-ol (commercially available). m/z (ES+): 417.5 (M+H).

Example 13

6-(2-Methoxy-ethoxy)-5-pyrrolidin-1-yl-pyrazine-2-carboxylic acid ((S)-1-hydroxymethyl-3-methyl-butyl)-amide a) 6-(2-Methoxy-ethoxy)-5-pyrrolidin-1-yl-pyrazine-2-carboxylic acid In analogy to the procedure described for the synthesis of 6-propoxy-5-pyrrolidin-1-yl-pyrazine-2-carboxylic acid (example 10, step c), the title compound was synthesized from 6-bromo-5-chloro-pyrazine-2-carboxylic acid methyl ester, 2-methoxy-ethanol (commercially available), pyrrolidine (commercially available) and subsequent saponification with KOH in 17% yield. m/z (ES$^+$): 268.0 (M+H).

b) 6-(2-Methoxy-ethoxy)-5-pyrrolidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-(2-methoxy-ethoxy)-5-pyrrolidin-1-yl-pyrazine-2-carboxylic acid and (S)-2-amino-4-methyl-pentan-1-ol (commercially available). m/z (ES$^+$): 367.3 (M+H).

Example 14

2-Ethyl-2-{[5-pyrrolidin-1-yl-6-(2,2,2-trifluoro-ethoxy)-pyrazine-2-carbonyl]-amino}-pentanoic acid methyl ester a) 5-Pyrrolidin-1-yl-6-(2,2,2-trifluoro-ethoxy)-pyrazine-2-carboxylic acid In analogy to the procedure described for the synthesis of 6-propoxy-5-pyrrolidin-1-yl-pyrazine-2-carboxylic acid (example 10, step c), the title compound was synthesized from 6-bromo-5-chloro-pyrazine-2-carboxylic acid methyl ester, 2,2,2-trifluoro-ethanol (commercially available), pyrrolidine (commercially available) and subsequent saponification with KOH in 41% yield. m/z (ES+): 292.0 (M+H).

b) 2-Ethyl-2-{[5-pyrrolidin-1-yl-6-(2,2,2-trifluoro-ethoxy)-pyrazine-2-carbonyl]-amino}-pentanoic acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-pyrrolidin-1-yl-6-(2,2,2-trifluoro-ethoxy)-pyrazine-2-carboxylic acid and 2-amino-2-ethyl-butyric acid methyl ester (as prepared in European Journal of Medicinal Chemistry 1984, 19, 261). m/z (ES$^+$): 419.3 (M+H).

Example 15

(S)-2-[(6-Cyclobutylmethoxy-5-pyrrolidin-1-yl-pyrazine-2-carbonyl)-amino]-propionic acid methyl ester The title compound was synthesized in analogy to Example 1, using 2-amino-3,5-dibromopyrazine, cyclobutyl-methanol, 1-bromo-4-chlorobutane and (S)-alanine methyl-ester as starting materials; yield 59.1 mg, 78%. LC@215 nm; Rt 2.33: 100%, m/z (ES$^+$): 377 (M+H).

Example 16

(R)-2-[(6-Cyclobutylmethoxy-5-pyrrolidin-1-yl-pyrazine-2-carbonyl)-amino]-propionic acid methyl ester The title compound was synthesized in analogy to Example 1, using 2-amino-3,5-dibromopyrazine, cyclobutyl-methanol, 1-bromo-4-chlorobutane and (R)-alanine methyl-ester as starting materials; yield 51.5 mg, 68%. LC@215 nm; Rt 2.43: 100%, m/z (ES$^+$): 377 (M+H).

Example 17

6-Cyclobutylmethoxy-5-pyrrolidin-1-yl-pyrazine-2-carboxylic acid ((S)-1-hydroxymethyl-3-methyl-butyl)-amide The title compound was synthesized in analogy to Example 1, using 2-amino-3,5-dibromopyrazine, cyclobutyl-methanol, 1-bromo-4-chlorobutane and (S)-leucinol as starting materials; yield 40.2 mg, 53%. LC@215 nm; Rt 2.31: 98%, m/z (ES$^+$): 363 (M+H).

Example 18

(S)-2-[(6-Cyclopentylmethoxy-5-pyrrolidin-1-yl-pyrazine-2-carbonyl)-amino]-propionic acid methyl ester The title compound was synthesized in analogy to Example 1, using 2-amino-3,5-dibromopyrazine, cyclopentyl-methanol, 1-bromo-4-chlorobutane and (S)-alanine methylester as starting materials; yield 22.1 mg, 26%. LC@215 nm; Rt 2.09: 100%, m/z (ES$^+$): 428 (M+H).

Example 19

(R)-2-[(6-Cyclopentylmethoxy-5-pyrrolidin-1-yl-pyrazine-2-carbonyl)-amino]-propionic acid methyl ester The title compound was synthesized in analogy to Example 1, using 2-amino-3,5-dibromopyrazine, cyclobutyl-methanol, 1-bromo-4-chlorobutane and (R)-alanine methylester as starting materials; yield 31.0 mg, 36%. LC@215 nm; Rt 2.03: 100%, m/z (ES$^+$): 429 (M+H).

Example 20

(S)-4-Methyl-2-{[6-(pyridin-2-ylmethoxy)-5-pyrrolidin-1-yl-pyrazine-2-carbonyl]-amino}-pentanoic acid methyl ester The title compound was synthesized in analogy to Example 1, using 2-amino-3,5-dibromopyrazine, 2-pyridinemethanol, 1-bromo-4-chlorobutane and (S)-leucine methylester as starting materials; yield 40.6 mg, 54%. LC@215 nm; Rt 2.43: 100%, m/z (ES$^+$): 377 (M+H).

Example 21

(S)-4-Methyl-2-{[6-(pyrimidin-2-ylmethoxy)-5-pyrrolidin-1-yl-pyrazine-2-carbonyl]-amino}-pentanoic acid methyl ester The title compound was synthesized in analogy to Example 1, using 2-amino-3,5-dibromopyrazine, 2-pyrimidinemethanol, 1-bromo-4-chlorobutane and (S)-leucine methylester as starting materials; yield 52.3 mg, 72%. LC@215 nm; Rt 2.31: 100%, m/z (ES+): 363 (M+H).

Example 22

2-Ethyl-2-[(6-isopropoxy-5-piperidin-1-yl-pyrazine-2-carbonyl)-amino]-butyric acid methyl ester a) 6-Bromo-5-piperidin-1-yl-pyrazine-2-carboxylic acid methyl ester A mixture of 2 g (9 mmol) 5-piperidin-1-yl-pyrazine-2-carboxylic acid methyl ester and 1.69 g (9.4 mmol) N-bromosuccinimid in 30 mL CHCl₃ was heated to 60° C. for 16 h. The mixture was concentrated and purified by flash column chromatography on silica eluting with a gradient formed from ethyl acetate and heptane to yield after evaporation of the product fractions 1.43 g (53%) of the title compound as white solid. m/z (ES⁺): 300.2 (M+H).

b) 6-Isopropoxy-5-piperidin-1-yl-pyrazine-2-carboxylic acid

A mixture of 0.212 g (0.707 mmol) 6-bromo-5-piperidin-1-yl-pyrazine-2-carboxylic acid methyl ester, 0.006 g (0.778 mmol) isopropanol and 0.034 g (0.778 mmol) NaH (55% dispersion in oil) in 1.7 mL dioxane was heated to 60° C. for 16 h. Water and 5N KOH was added and the mixture was heated to 50° C. for 4 h. Formic acid and DMF was added and the mixture was subjected to purification by preparative HPLC on reversed phase eluting with a gradient formed from acetonitrile, water and formic acid. The product fractions were combined and evaporated to yield 0.04 g (21%) of the title compound. m/z (ES+): 266.4 (M+H).

c) 2-Ethyl-2-[(6-isopropoxy-5-piperidin-1-yl-pyrazine-2-carbonyl)-amino]-butyric acid methyl ester In analogy to the procedure described for the synthesis of 6-Propoxy-5-pyrrolidin-1-yl-pyrazine-2-carboxylic acid ((S)-1-hydroxymethyl-3-methyl-butyl)-amide (example 10, step d) the title compounds was prepared from 6-Isopropoxy-5-piperidin-1-yl-pyrazine-2-carboxylic acid and 2-amino-2-ethyl-butyric acid methyl ester (European Journal of Medicinal Chemistry 1984, 19, 261). m/z (ES⁺): 393.3 (M+H).

Example 23

6-(2,2-Dimethyl-propoxy)-5-piperidin-1-yl-pyrazine-2-carboxylic acid ((S)-1-hydroxymethyl-3-methyl-butyl)-amide a) 6-(2,2-Dimethyl-propoxy)-5-piperidin-1-yl-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-piperidin-1-yl-pyrazine-2-carboxylic acid methyl ester, 2,2-dimethyl-propan-1-ol and subsequent saponification with KOH in 35% yield. m/z (ES⁺): 294.3 (M+H).

b) 6-(2,2-Dimethyl-propoxy)-5-piperidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 6-(2,2-dimethyl-propoxy)-5-piperidin-1-yl-pyrazine-2-carboxylic acid and (S)-2-amino-4-methyl-pentan-1-ol (commercially available). m/z (ES⁺): 393.4 (M+H).

Example 24

6-(2-Methoxy-ethoxy)-5-piperidin-1-yl-pyrazine-2-carboxylic acid ((S)-1-hydroxymethyl-3-methyl-butyl)-amide a) 6-(2-Methoxy-ethoxy)-5-piperidin-1-yl-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-piperidin-1-yl-pyrazine-2-carboxylic acid methyl ester, 2-methoxy ethanol (commercially available) and subsequent saponification with KOH in 66% yield. m/z (ES⁺): 282.4 (M+H).

b) 6-(2-Methoxy-ethoxy)-5-piperidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 6-(2-methoxy-ethoxy)-5-piperidin-1-yl-pyrazine-2-carboxylic acid and (S)-2-amino-4-methyl-pentan-1-ol (commercially available). m/z (ES⁺): 381.5 (M+H).

Example 25

(S)-2-{[6-(2-Methoxy-ethoxy)-5-piperidin-1-yl-pyrazine-2-carbonyl]-amino}-4-methyl-pentanoic acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-(2-methoxy-ethoxy)-5-piperidin-1-yl-pyrazine-2-carboxylic acid and (S)-leucine methyl ester (commercially available). m/z (ES⁺): 409.3 (M+H).

Example 26

2-Ethyl-2-{[5-morpholin-4-yl-6-(2,2,2-trifluoro-ethoxy)-pyrazine-2-carbonyl]-amino}-butyric acid methyl ester a) 5-Morpholin-4-yl-pyrazine-2-carboxylic acid methyl ester A mixture of 4.9 g (28 mmol) 5-chloro-pyrazine-2-carboxylic acid methyl ester (commercially available), 3.2 g (37 mmol) morpholine and 7.37 g (73 mmol) NEt₃ in 50 mL dioxane was heated to 45° C. for 16 h. Water and NaCl aq. was added and the mixture was extracted with ethyl acetate. The combined organic layers were washed with NaCl aq., dried with MgSO₄, filtered and evaporated. The residue was recrystallized from ethyl acetate to yield 5.65 g (89%) of the title compound as white solid. m/z (ES⁺): 224.3 (M+H).

b) 6-Bromo-5-morpholin-4-yl-pyrazine-2-carboxylic acid methyl ester

In analogy to the procedure described for the synthesis of 6-bromo-5-piperidin-1-yl-pyrazine-2-carboxylic acid methyl ester (example 22, step a) the title compound was synthesized from 5-morpholin-4-yl-pyrazine-2-carboxylic acid methyl ester and NBS. m/z (ES⁺): 302.1 (M+H).

c) 5-Morpholin-4-yl-6-(2,2,2-trifluoro-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-morpholin-4-yl-pyrazine-2-carboxylic acid methyl ester, 2,2,2-trifluoroethanol (commercially available) and subsequent saponification with KOH in 58% yield. m/z (ES⁺): 308.4 (M+H).

d) 2-Ethyl-2-{[5-morpholin-4-yl-6-(2,2,2-trifluoro-ethoxy)-pyrazine-2-carbonyl]-amino}-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-morpholin-4-yl-6-(2,2,2-trifluoro-ethoxy)-pyrazine-2-carboxylic acid and 2-amino-2-ethyl-butyric acid methyl ester (European Journal of Medicinal Chemistry 1984, 19, 261). m/z (ES⁺): 435.1 (M+H).

Example 27

(S)-4-Methyl-2-{[5-morpholin-4-yl-6-(2,2,2-trifluoro-ethoxy)-pyrazine-2-carbonyl]-amino}-pentanoic acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-morpholin-4-yl-6-(2,2,2-trifluoro-ethoxy)-pyrazine-2-carboxylic acid and (S)-leucine methyl ester (commercially available). m/z (ES⁺): 435.3 (M+H).

Example 28

6-(2,2-Dimethyl-propoxy)-5-morpholin-4-yl-pyrazine-2-carboxylic acid ((S)-1-hydroxymethyl-3-methyl-butyl)-amide a) 6-(2,2-Dimethyl-propoxy)-5-morpholin-4-yl-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-morpholin-4-yl-pyrazine-2-carboxylic acid methyl ester, 2,2-dimethyl-propan-1-ol (commercially available) and subsequent saponification with KOH in 31% yield. m/z (ES⁺): 296.5 (M+H).

b) 6-(2,2-Dimethyl-propoxy)-5-morpholin-4-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-(2,2-dimethyl-propoxy)-5-morpholin-4-yl-pyrazine-2-carboxylic acid and (S)-leucinol (commercially available). m/z (ES⁺): 395.3 (M+H).

Example 29

2-Ethyl-2-{[6-(2-methoxy-ethoxy)-5-morpholin-4-yl-pyrazine-2-carbonyl]-amino}-butyric acid methyl ester a) 6-(2-Methoxy-ethoxy)-5-morpholin-4-yl-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-morpholin-4-yl-pyrazine-2-carboxylic acid methyl ester, 2-methoxy ethanol (commercially available) and subsequent saponification with KOH in 73% yield. m/z (ES⁺): 284.4 (M+H).

b) 2-Ethyl-2-{[6-(2-methoxy-ethoxy)-5-morpholin-4-yl-pyrazine-2-carbonyl]-amino}-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-(2-methoxy-ethoxy)-5-morpholin-4-yl-pyrazine-2-carboxylic acid and 2-amino-2-ethyl-butyric acid methyl ester (European Journal of Medicinal Chemistry 1984, 19, 261). m/z (ES⁺): 411.5 (M+H).

Example 30

2-{[5-Cyclohexylamino-6-(2,2,2-trifluoro-ethoxy)-pyrazine-2-carbonyl]-amino}-2-ethyl-butyric acid methyl ester a) 5-Cyclohexylamino-pyrazine-2-carboxylic acid methyl ester In analogy to the procedure described for the synthesis of 5-morpholin-4-yl-pyrazine-2-carboxylic acid methyl ester (example 26, step a)), the title compound was prepared from 5-chloro-pyrazine-2-carboxylic acid methyl ester (commercially available), and cyclohexylamine (commercially available). m/z (ES⁺): 236.4 (M+H).

b) 6-Bromo-5-cyclohexylamino-pyrazine-2-carboxylic acid methyl ester

In analogy to the procedure described for the synthesis of 6-bromo-5-piperidin-1-yl-pyrazine-2-carboxylic acid methyl ester (example 22, step a) the title compound was synthesized from 5-cyclohexylamino-pyrazine-2-carboxylic acid methyl ester and NBS. m/z (ES⁺): 314.2 (M+H).

c) 5-Cyclohexylamino-6-(2,2,2-trifluoro-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-cyclohexylamino-pyrazine-2-carboxylic acid methyl ester, 2,2,2-trifluoroethanol (commercially available) and subsequent saponification with KOH in 55% yield. m/z (ES$^+$): 320.4 (M+H).

d) 2-{[5-Cyclohexylamino-6-(2,2,2-trifluoro-ethoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-cyclohexylamino-6-(2,2,2-trifluoro-ethoxy)-pyrazine-2-carboxylic acid and 2-amino-2-ethyl-butyric acid methyl ester (European Journal of Medicinal Chemistry 1984, 19, 261). m/z (ES$^+$): 447.5 (M+H).

Example 31

2-{[5-Cyclohexylamino-6-(2,2-dimethyl-propoxy)-pyrazine-2-carbonyl]-amino}-2-ethyl-butyric acid methyl ester a) 5-Cyclohexylamino-6-(2,2-dimethyl-propoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-cyclohexylamino-pyrazine-2-carboxylic acid methyl ester, 2,2-dimethyl-propan-1-ol (commercially available) and subsequent saponification with KOH in 5% yield. m/z (ES$^+$): 308.4 (M+H).

b) 2-{[5-Cyclohexylamino-6-(2,2-dimethyl-propoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-cyclohexylamino-6-(2,2-dimethyl-propoxy)-pyrazine-2-carboxylic acid and 2-amino-2-ethyl-butyric acid methyl ester (European Journal of Medicinal Chemistry 1984, 19, 261). m/z (ES$^+$): 435.4 (M+H).

Example 32

2-{[5-Cyclohexylamino-6-(2-methoxy-ethoxy)-pyrazine-2-carbonyl]-amino}-2-ethyl-butyric acid methyl ester a) 5-Cyclohexylamino-6-(2-methoxy-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-cyclohexylamino-pyrazine-2-carboxylic acid methyl ester, 2-methoxy ethanol (commercially available) and subsequent saponification with KOH in 65% yield. m/z (ES$^+$): 296.4 (M+H).

b) 2-{[5-Cyclohexylamino-6-(2-methoxy-ethoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-cyclohexylamino-6-(2-methoxy-ethoxy)-pyrazine-2-carboxylic acid and 2-amino-2-ethyl-butyric acid methyl ester (European Journal of Medicinal Chemistry 1984, 19, 261). m/z (ES$^+$): 423.4 (M+H).

Example 33

2-{[5-Butylamino-6-(2,2,2-trifluoro-ethoxy)-pyrazine-2-carbonyl]-amino}-2-ethyl-butyric acid methyl ester a) 5-Butylamino-pyrazine-2-carboxylic acid methyl ester

In analogy to the procedure described for the synthesis of 5-morpholin-4-yl-pyrazine-2-carboxylic acid methyl ester (example 26, step a)), the title compound was prepared from 5-chloro-pyrazine-2-carboxylic acid methyl ester (commercially available), and butylamine (commercially available). m/z (ES$^+$): 210.3 (M+H).

b) 6-Bromo-5-butylamino-pyrazine-2-carboxylic acid methyl ester

In analogy to the procedure described for the synthesis of 6-bromo-5-piperidin-1-yl-pyrazine-2-carboxylic acid methyl ester (example 22, step a) the title compound was synthesized from 5-butylamino-pyrazine-2-carboxylic acid methyl ester and NBS. m/z (ES$^+$): 288.1 (M+H).

c) 5-Butylamino-6-(2,2,2-trifluoro-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-butylamino-pyrazine-2-carboxylic acid methyl ester, 2,2,2-trifluoroethanol (commercially available) and subsequent saponification with KOH in 25% yield. m/z (ES$^+$): 294.3 (M+H).

d) 2-{[5-Butylamino-6-(2,2,2-trifluoro-ethoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-butylamino-6-(2,2,2-trifluoro-ethoxy)-pyrazine-2-carboxylic acid and 2-amino-2-ethyl-butyric acid methyl ester (European Journal of Medicinal Chemistry 1984, 19, 261). m/z (ES$^+$): 421.1 (M+H).

Example 34

2-{[5-Butylamino-6-(2-methoxy-ethoxy)-pyrazine-2-carbonyl]-amino}-2-ethyl-butyric acid methyl ester a) 5-Butylamino-6-(2-methoxy-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-butylamino-pyrazine-2-carboxylic acid methyl ester, 2-methoxyethanol (commercially available) and subsequent saponification with KOH in 42% yield. m/z (ES$^+$): 270.3 (M+H).

b) 2-{[5-Butylamino-6-(2-methoxy-ethoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-butylamino-6-(2-methoxy-ethoxy)-pyrazine-2-carboxylic acid and 2-amino-2-ethyl-butyric. acid methyl ester (European Journal of Medicinal Chemistry 1984, 19, 261). m/z (ES$^+$): 397.1 (M+H).

Example 35

2-[(5-Diethylamino-6-isopropoxy-pyrazine-2-carbonyl)-amino]-2-ethyl-butyric acid methyl ester a) 5-Diethylamino-pyrazine-2-carboxylic acid methyl ester

In analogy to the procedure described for the synthesis of 5-morpholin-4-yl-pyrazine-2-carboxylic acid methyl ester (example 26, step a)), the title compound was prepared from 5-chloro-pyrazine-2-carboxylic acid methyl ester (commercially available) and diethylamine (commercially available). m/z (ES$^+$): 210.3 (M+H).

b) 6-Bromo-5-diethylamino-pyrazine-2-carboxylic acid methyl ester

In analogy to the procedure described for the synthesis of 6-bromo-5-piperidin-1-yl-pyrazine-2-carboxylic acid methyl ester (example 22, step a) the title compound was synthesized from 5-diethylamino-pyrazine-2-carboxylic acid methyl ester and NBS. m/z (ES$^+$): 288.1 (M+H).

c) 5-Diethylamino-6-isopropoxy-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-bromo-5-diethylamino-pyrazine-2-carboxylic acid methyl ester, isopropanol (commercially available) and subsequent saponification with KOH in 16% yield. m/z (ES$^+$): 254.4 (M+H).

d) 2-[(5-Diethylamino-6-isopropoxy-pyrazine-2-carbonyl)-amino]-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 5-diethylamino-6-isopropoxy-pyrazine-2-carboxylic acid and 2-amino-2-ethyl-butyric acid methyl ester (European Journal of Medicinal Chemistry 1984, 19, 261). m/z (ES$^+$): 381.2 (M+H).

Example 36

5-Diethylamino-6-(2-methoxy-ethoxy)-pyrazine-2-carboxylic acid ((S)-1-hydroxymethyl-3-methyl-butyl)-amide a) 5-Diethylamino-6-(2-methoxy-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 6-Bromo-5-diethylamino-pyrazine-2-carboxylic acid methyl ester, 2-methoxy ethanol (commercially available) and subsequent saponification with KOH in 76% yield. m/z (ES$^+$): 270.5 (M+H).

b) 5-Diethylamino-6-(2-methoxy-ethoxy)-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-diethylamino-6-(2-methoxy-ethoxy)-pyrazine-2-carboxylic acid and (S)-leucinol (commercially available). m/z (ES$^+$): 369.2 (M+H).

Example 37

(S)-2-{[5-Diethylamino-6-(2-methoxy-ethoxy)-pyrazine-2-carbonyl]-amino}-4-methyl-pentanoic acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-diethylamino-6-(2-methoxy-ethoxy)-pyrazine-2-carboxylic acid and (S)-leucine methyl ester (commercially available). m/z (ES$^+$): 397.1 (M+H).

Example 38

5-Diethylamino-6-(2-methoxy-ethoxy)-pyrazine-2-carboxylic acid ((S)-1-carbamoyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-diethylamino-6-(2-methoxy-ethoxy)-pyrazine-2-carboxylic acid and L-leucine amide (commercially available). m/z (ES$^+$): 382.1 (M+H).

Example 39

2-{[5-(4,4-Difluoro-piperidin-1-yl)-6-(2,2-dimethyl-propoxy)-pyrazine-2-carbonyl]-amino}-2-ethyl-butyric acid methyl ester a) 5-(4,4-Difluoro-piperidin-1-yl)-pyrazine-2-carboxylic acid methyl ester In analogy to the procedure described for the synthesis of 5-morpholin-4-yl-pyrazine-2-carboxylic acid methyl ester (example 26, step a)), the title compound was prepared from 5-chloro-pyrazine-2-carboxylic acid methyl ester (commercially available), and 4,4-difluoro-piperidine (commercially available). m/z (ES+): 258.3 (M+H).

b) 6-Bromo-5-(4,4-difluoro-piperidin-1-yl)-pyrazine-2-carboxylic acid methyl ester In analogy to the procedure described for the synthesis of 6-bromo-5-piperidin-1-yl-pyrazine-2-carboxylic acid methyl ester (example 22, step a) the title compound was synthesized from 5-(4,4-difluoro-piperidin-1-yl)-pyrazine-2-carboxylic acid methyl ester and NBS. m/z (ES$^+$): 336.2 (M+H).

c) 5-(4,4-Difluoro-piperidin-1-yl)-6-(2,2-dimethyl-propoxy)-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-(4,4-difluoro-piperidin-1-yl)-pyrazine-2-carboxylic acid methyl ester, 2,2-dimethyl propanol (commercially available) and subsequent saponification with KOH in 24% yield. m/z (ES$^+$): 330.3 (M+H).

d) 2-{[5-(4,4-Difluoro-piperidin-1-yl)-6-(2,2-dimethyl-propoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-(4,4-difluoro-piperidin-1-yl)-6-(2,2-dimethyl-propoxy)-pyrazine-2-carboxylic acid and 2-amino-2-ethyl-butyric acid methyl ester (European Journal of Medicinal Chemistry 1984, 19, 261). m/z (ES$^+$): 457.3 (M+H).

Example 40

6-Cyclopentylmethoxy-5-(4,4-difluoro-piperidin-1-yl)-pyrazine-2-carboxylic acid ((S)-1-hydroxymethyl-3-methyl-butyl)-amide a) 6-Cyclopentylmethoxy-5-(4,4-difluoro-piperidin-1-yl)-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-(4,4-difluoro-piperidin-1-yl)-pyrazine-2-carboxylic acid methyl ester, cyclopentylmethanol (commercially available) and subsequent saponification with KOH in 40% yield. m/z (ES+): 342.1 (M+H).

b) 6-Cyclopentylmethoxy-5-(4,4-difluoro-piperidin-1-yl)-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-cyclopentylmethoxy-5-(4,4-difluoro-piperidin-1-yl)-pyrazine-2-carboxylic acid and (S)-leucinol (commercially available). m/z (ES$^+$): 441.3 (M+H).

Example 41

(S)-2-{[6-Cyclopentylmethoxy-5-(4,4-difluoro-piperidin-1-yl)-pyrazine-2-carbonyl]-amino}-4-methyl-pentanoic acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compounds was prepared from 6-cyclopentylmethoxy-5-(4,4-difluoro-piperidin-1-yl)-pyrazine-2-carboxylic acid and (S)-leucine methyl ester (commercially available). m/z (ES$^+$): 469.1 (M+H).

Example 42

2-{[5-(4,4-Difluoro-piperidin-1-yl)-6-(2-methoxy-ethoxy)-pyrazine-2-carbonyl]-amino}-2-ethyl-butyric acid methyl ester a) 5-(4,4-Difluoro-piperidin-1-yl)-6-(2-methoxy-ethoxy)-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-(4,4-difluoro-piperidin-1-yl)-pyrazine-2-carboxylic acid methyl ester, 2-methoxy ethanol (commercially available) and subsequent saponification with KOH in 61% yield. m/z (ES$^+$): 318.3 (M+H).

b) 2-{[5-(4,4-Difluoro-piperidin-1-yl)-6-(2-methoxy-ethoxy)-pyrazine-2-carbonyl]-amino}-2-ethyl-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-(4,4-difluoro-piperidin-1-yl)-6-(2-methoxy-ethoxy)-pyrazine-2-carboxylic acid and 2-amino-2-ethyl-butyric acid methyl ester (European Journal of Medicinal Chemistry 1984, 19, 261). m/z (ES$^+$): 445.1 (M+H).

Example 43

2-Ethyl-2-{[6-piperidin-1-yl-5-(2,2,2-trifluoro-ethoxy)-pyrazine-2-carbonyl]-amino}-butyric acid methyl ester a) 5-Chloro-6-piperidin-1-yl-pyrazine-2-carboxylic acid methyl ester From a mixture of 1 g (3.98 mmol) 6-bromo-5-chloro-pyrazine-2-carboxylic acid and 0.508 g (5.97 mmol) piperidine in 1 mL DMF 0.61 g (60%) of the title compound were filtered off as slightly yellow crystals. m/z (ES$^+$): 256.4 (M+H).

b) 6-Piperidin-1-yl-5-(2,2,2-trifluoro-ethoxy)-pyrazine-2-carboxylic acid

In analogy to the procedure described for the synthesis of 6-isopropoxy-5-piperidin-1-yl-pyrazine-2-carboxylic acid (example 22, step b)) the title compound was synthesized from 5-chloro-6-piperidin-1-yl-pyrazine-2-carboxylic acid methyl ester, 2,2,2-trifluoro-ethanol (commercially available) and subsequent saponification with KOH in 56% yield. m/z (ES$^+$): 306.3 (M+H).

c) 2-Ethyl-2-{[6-piperidin-1-yl-5-(2,2,2-trifluoro-ethoxy)-pyrazine-2-carbonyl]-amino}-butyric acid methyl ester In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 6-piperidin-1-yl-5-(2,2,2-trifluoro-ethoxy)-pyrazine-2-carboxylic acid and 2-amino-2-ethyl-butyric acid methyl ester (European Journal of Medicinal Chemistry 1984, 19, 261). m/z (ES$^+$): 433.5 (M+H).

Example 44

5-Cyclopropylmethoxy-6-piperidin-1-yl-pyrazine-2-carboxylic acid ((S)-1-hydroxymethyl-3-methyl-butyl)-amide a) 5-Cyclopropylmethoxy-6-piperidin-1-yl-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 5-chloro-6-piperidin-1-yl-pyrazine-2-carboxylic acid methyl ester, cyclopropyl methanol (commercially available) and subsequent saponification with KOH in 11% yield. m/z (ES$^+$): 2781 (M+H).

b) 5-Cyclopropylmethoxy-6-piperidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 5-cyclopropylmethoxy-6-piperidin-1-yl-pyrazine-2-carboxylic acid and (S)-leucinol (commercially available). m/z (ES$^+$): 377.4 (M+H).

Example 45

6-[(2-Methoxy-ethyl)-methyl-amino]-5-piperidin-1-yl-pyrazine-2-carboxylic acid ((S)-1-hydroxymethyl-3-methyl-butyl)-amide a) 6-[(2-Methoxy-ethyl)-methyl-amino]-5-piperidin-1-yl-pyrazine-2-carboxylic acid In analogy to the procedure described for the synthesis of 6-isopropoxy-5-piperidin-1-yl-pyrazine-2-carboxylic acid (example 22, step b)) the title compound was synthesized from 6-bromo-5-piperidin-1-yl-pyrazine-2-carboxylic acid methyl ester, (2-Methoxy-ethyl)-methyl-amine and subsequent saponification with KOH. m/z (ES$^+$): 295.2 (M+H).

b) 6-[(2-Methoxy-ethyl)-methyl-amino]-5-piperidin-1-yl-pyrazine-2-carboxylic acid ((S)-1-hydroxymethyl-3-methyl-butyl)-amide In analogy to the procedure described for the synthesis of 6-propoxy-5-pyrrolidin-1-yl-pyrazine-2-carboxylic acid ((S)-1-hydroxymethyl-3-methyl-butyl)-amide (example 10, step d) the title compound was prepared from 6-[(2-Methoxy-ethyl)-methyl-amino]-5-piperidin-1-yl-pyrazine-2-carboxylic acid and (S)-2-Amino-4-methyl-pentan-1-ol (commercially available). m/z (ES$^+$): 394.3 (M+H).

Example 46

2-{[6-(4-Fluoro-phenyl)-5-piperidin-1-yl-pyrazine-2-carbonyl]-amino}-2-methyl-propionic acid methyl ester a) 5-Bromo-3-(4-fluoro-phenyl)-pyrazin-2-ylamine Tetrakis (triphenylphosphine) palladium (0) (1.12 g, 0.97 mmol, 0.05 eq) was added portion-wise to a solution of 2-amino-3,5-dibromopyrazine (5.01 g, 19.76 mmol, 1.0 eq) in 1,2-dimethoxyethane (100 ml) at room temperature and the reaction stirred for 0.5 hours. A solution of sodium carbonate (5.30 g, 50.5 mmol, 2.6 eq) in water (50 ml) was added portion-wise to the resulting mixture, followed by 4-fluorophenylboronic acid (3.08 g, 21.9 mmol, 1.1 eq). The mixture was heated to 100° C. for 5 h. The resulting yellow solution was partitioned between 10% aqueous citric acid (25 ml) and ethyl acetate (50 ml). The organic layer was washed with 10% aqueous sodium bicarbonate (25 ml), brine (25 ml), dried over magnesium sulfate and concentrated in vacuo. The residue was purified by chromatography on silica gel with a gradient of heptane to dichloromethane to afford 5-Bromo-3-(4-fluoro-phenyl)-pyrazin-2-ylamine as white crystals. Yield=3.22 g (60%). HPLC-MS=100%; 1.89 min (M+1=270.1).

b) 5-Amino-6-(4-fluoro-phenyl)-pyrazine-2-carboxylic acid methyl ester

To a methanol solution (35 ml) of 5-bromo-3-(4-fluoro-phenyl)-pyrazin-2-ylamine (1.87 g, 6.97 mmol, 1.0 eq) was added 15 ml ethyl acetate at room temperature. [1,1'-bis(diphenylphosphino) ferrocen]palladium(II)chloride 1:1 complex with dichloromethane (0.26 g, 0.32 mmol, 0.05 eq) was added portion-wise to the reaction mixture followed by triethylamine (1.95 ml, 13.5 mmol, 2.0 eq) and the solution was heated with stirring to 110° C. under 70 bar carbon monoxide for 18 hours. On cooling and removal of carbon monoxide, the reaction mixture was concentrated in vacuo and the residue purified by chromatography on silica gel with heptane:ethyl acetate (1:1) to afford 5-amino-6-(4-fluoro-phenyl)-pyrazine-2-carboxylic acid methyl ester as white crystals. Yield=1.26 g (73%). $^1$H-NMR (400 MHz, DMSO): δ 3.80 (3H, s), 7.11 (2H, br s), 7.33 (2H, t, J=8.87 Hz), 7.67-7.70 (2H, m), 8.56 (1H, s). HPLC-MS=100%; 1.49 min (MW=247; M+1=248.3).

c) 5-Bromo-6-(4-fluoro-phenyl)-pyrazine-2-carboxylic acid methyl ester

To a suspension of 5-amino-6-(4-fluoro-phenyl)-pyrazine-2-carboxylic acid methyl ester (1.26 g, 5.10 mmol, 1.0 eq) in dibromomethane (25 ml) was added isoamyl nitrite (0.85 ml, 6.29 mmol, 1.2 eq) at room temperature. The resulting suspension was added over 30 minutes at room temperature to a dibromomethane (5 ml) solution of trimethylbromosilane (0.82 ml, 5.90 mmol, 1.15 eq). The mixture was stirred for 2 hours at room temperature after which time the turbid solution was added to aqueous sodium bicarbonate (10%, 15 ml). The phases were mixed, separated and the organic layer dried over magnesium sulfate, concentrated in vacuo and purified by chromatography on silica gel using a gradient of heptane to 10% ethyl acetate in heptane to afford 5-Bromo-6-(4-fluoro-phenyl)-pyrazine-2-carboxylic acid methyl ester as white crystals. Yield=0.81 g (51%). $^1$H NMR (250 MHz, DMSO): δ 3.92 (3H, s), 7.38 (2H, t, J=8.98 Hz), 7.76-7.81 (2H, m), 8.98 (1H, s). HPLC-MS=100%; 2.13 min (MW=311; M+1=313.0).

d) 6-(4-Fluoro-phenyl)-5-piperidin-1-yl-pyrazine-2-carboxylic acid methyl ester

Piperidine (0.48 ml, 4.82 mmol, 2.0 eq) was added portion-wise to a acetonitrile (2 ml) solution of 5-bromo-6-(4-fluoro-phenyl)-pyrazine-2-carboxylic acid methyl ester (0.75 g, 2.41 mmol, 1.0 eq) at room temperature. The mixture was irradiated at 100° C. in a microwave with stirring for 30 minutes. HPLC-MS indicated complete consumption of starting material. The crude mixture was cooled to room temperature concentrated. The residue was re-dissolved in ethyl acetate (10 ml), washed with water (5 ml) and the organic phase dried over MgSO$_4$. Following filtration and evaporation in vacuo, the residue was purified by chromatography on silica gel using a gradient of heptane to 10% ethyl acetate in heptane to afford 6-(4-fluoro-phenyl)-5-piperidin-1-yl-pyrazine-2-carboxylic acid methyl ester. Yield=0.48 g (63%). $^1$H NMR (250 MHz, CDCl$_3$): δ 1.42-1.53 (6H, m), 3.20-3.24 (4H, m), 3.88 (3H, s), 7.06 (2H, t, J=8.78 Hz), 7.74-7.80 (2H, m), 8.68 (1H, s).

e) 6-(4-Fluoro-phenyl)-5-piperidin-1-yl-pyrazine-2-carboxylic acid

To a tetrahydrofuran (5 ml) solution of 6-(4-fluoro-phenyl)-5-piperidin-1-yl-pyrazine-2-carboxylic acid methyl ester (0.48 g, 1.52 mmol, 1.0 eq) was added a solution of lithium hydroxide (1M, 1.52 ml, 1.52 mmol, 1.0 eq) in water. The mixture was stirred overnight at room temperature after which time the resulting solution was acidified with hydrochloric acid (pH~5) and aqueous phase extracted with ethyl acetate (2×10 ml). The organic phase was dried over magnesium sulfate and concentrated in vacuo to afford 6-(4-fluoro-phenyl)-5-piperidin-1-yl-pyrazine-2-carboxylic acid as white crystals. Yield=0.42 g (91%). $^1$H NMR (400 MHz, DMSO): δ 1.46-1.53 (6H, m), 3.22-3.25 (4H, m), 7.32 (2H, t, J=8.87 Hz), 7.82-7.86 (2H, m), 8.62 (1H, s).

f) 2-{[6-(4-Fluoro-phenyl)-5-piperidin-1-yl-pyrazine-2-carbonyl]-amino}-2-methyl-propionic acid methyl ester To a dichloromethane (1 ml) solution of 6-(4-fluoro-phenyl)-5-piperidin-1-yl-pyrazine-2-carboxylic acid (0.107 g, 0.358 mmol, 1.0 eq) was added oxalyl chloride (0.136 g, 1.07 mmol, 3.0 eq). The reaction was stirred at room temperature for 3 hours after which time the solvent was removed in vacuo. The residue was re-dissolved in dichloromethane (3 ml) and added portion-wise to a dichloromethane (1 ml) solution of aminoisobutyric acid methyl ester (0.066 g, 0.429 mmol, 1.2 eq). PS—N,N-diisopropylethylamine (0.31 g, 1.04 mmol, 3.0 eq) resin was added to the reaction and the mixture stirred overnight at room temperature. PS-isocyanate (0.15 g, 0.358 mmol, 1.0 eq) and PS-aminomethyl (0.15 g, 0.358 mmol, 1.0 eq) resin were added to the reaction and the mixture stirred for a further 12 hrs at room temperature. The reaction was filtered and resin washed successfully with dichloromethane (2×3 ml). The combined filtrates were concentrated in vacuo and the residue purified by chromatography on silica gel with heptane:ethyl acetate (1:1) to afford 2-{[6-(4-fluoro-phenyl)-5-piperidin-1-yl-pyrazine-2-carbonyl]-amino}-2-methyl-propionic acid methyl ester. Yield=0.030 g (21%). HPLC-MS=100%; 2.52 min (MW=400; M+1=401.2).

Example 47

2-{[6-(4-Chloro-phenyl)-5-pyrrolidin-1-yl-pyrazine-2-carbonyl]-amino}-2-methyl-propionic acid methyl ester The title compound was synthesized in analogy to Example 46 a to f, using 2-amino-3,5-dibromopyrazine, 4-chlorophenylboronic acid, pyrrolidine and aminoisobutyric acid methyl ester as starting materials; yield 5.5 mg. HPLC-MS=100%; 2.42 min (MW=402; M+1=403.1).

Example 48

2-{[5-Cyclopropylmethoxy-6-(4-fluoro-phenyl)-pyrazine-2-carbonyl]-amino}-2-methyl-propionic acid methyl ester a) 5-Bromo-6-(4-fluoro-phenyl)-pyrazine-2-carboxylic acid methyl ester was prepared as described in Example 46 a to c b) 6-(4-Chloro-phenyl)-5-cyclopropylmethoxy-pyrazine-2-carboxylic acid Cyclopropyl-methanol (2.2 g, 30.6 mmol, 10.0 eq) was dissolved in dry tetrahydrofuran (10 ml, 20 vol) and potassium tert-butoxide (3.4 g, 30.6 mmol, 10.0 eq) added portion-wise. After stirring for 15 minutes at room temperature 5-bromo-6-(4-fluoro-phenyl)-pyrazine-2-carboxylic acid methyl ester (0.95 g, 3.06 mmol, 1.0 eq) was added drop-wise as a tetrahydrofuran (10 ml) solution. The reaction mixture was stirred overnight at room temperature or until deemed complete by HPLC-MS analysis. The solution was concentrated in vacuo and the residue re-dissolved in ethyl acetate (20 ml). The resulting solution was washed with water (5 ml) and the aqueous phase extracted with ethyl acetate (10 ml). The combined organic phases were dried over magnesium sulphate, filtered and concentrated in vacuo to afford 6-(4-fluoro-phenyl)-5-cyclopropylmethoxy-pyrazine-2-carboxylic acid. Yield=0.89 g (75%).

c) 2-{[5-Cyclopropylmethoxy-6-(4-fluoro-phenyl)-pyrazine-2-carbonyl]-amino}-2-methyl-propionic acid methyl ester The title compound was synthesized in analogy to Example 46 e to f, using 26-(4-fluoro-phenyl)-5-cyclopropylmethoxy-pyrazine-2-carboxylic acid and aminoisobutyric acid methyl ester as starting materials; yield 5.4 mg. HPLC-MS=100%; 2.51 min (MW=387; M+1=388.1).

Example 49

(R)-2-{[6-(4-Chloro-phenyl)-5-(2,2,2-trifluoro-ethoxy)-pyrazine-2-carbonyl]-amino}-3-methyl-butyric acid methyl ester The title compound was synthesized in analogy to Example 48 a to c, using 2-amino-3,5-dibromopyrazine, 4-chlorophenylboronic acid, 2,2,2-trifluoroethanol and (R)-valine methyl ester as starting materials; yield 6.0 mg. HPLC-MS=98%; 2.64 min (MW=445; M+1=446.1).

Example 50

(R)-2-{[6-(3-Chloro-phenyl)-5-(2,2,2-trifluoro-ethoxy)-pyrazine-2-carbonyl]-amino}-3-methyl-butyric acid methyl ester The title compound was synthesized in analogy to Example 48 a to c, using 2-amino-3,5-dibromopyrazine, 3-chlorophenylboronic acid, 2,2,2-trifluoroethanol and (R)-valine methyl ester as starting materials; yield 6.4 mg. HPLC-MS=97%; 2.48 min (MW=445; M+1=446.1).

Example 51

(R)-2-{[6-(3-Chloro-phenyl)-5-cyclopropylmethoxy-pyrazine-2-carbonyl]-amino}-3-methyl-butyric acid methyl ester The title compound was synthesized in analogy to Example 48 a to c, using 2-amino-3,5-dibromopyrazine, 3-chlorophenylboronic acid, cyclopropyl-methanol and (R)-valine methyl ester as starting materials; yield 6.5 mg. HPLC-MS=100%; 2.75 min (MW=417; M+1=418.1).

Example 52

2-{[6-(4-Chloro-phenyl)-5-cyclopropylmethoxy-pyrazine-2-carbonyl]-amino}-2-methyl-propionic acid methyl ester The title compound was synthesized in analogy to Example 48 a to c, using 2-amino-3,5-dibromopyrazine, 4-chlorophenylboronic acid, cyclopropyl-methanol and aminoisobutyric acid methyl ester as starting materials; yield 6.0 mg. HPLC-MS=100%; 2.64 min (MW=403; M+1=404.1).

GALENICAL EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound of the formula:

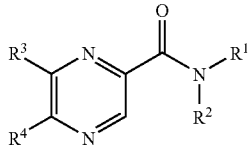

or a pharmaceutically acceptable salt thereof, wherein:
(a) $R_2$ is hydrogen and $R_1$ is selected from the group consisting of:
  (1) lower alkyl,
  (2) lower hydroxyalkyl,
  (3) cycloalkyl, which is optionally substituted by a substituent selected from the group consisting of hydroxy, lower alkoxy and lower hydroxyalkyl,
  (4) lower cycloalkylalkyl,
  (5) lower heterocyclylalkyl,
  (6) —$CR^5R^6$—$COOR^7$, and
  (7) —$CR^5R^6$—$CONH_2$;
(b) one of $R^3$ and $R^4$ is —$OR^8$ and the other one of $R^3$ and $R^4$ is selected from the group consisting of:
  (1) lower alkylamino,
  (2) lower dialkylamino,
  (3) cycloalkylamino, and
  (4) a heterocyclic ring selected from the group consisting of azetidinyl, pyrrolidinyl, piperidinyl, morpholinyl, thiomorpholinyl and azepanyl, wherein said heterocyclic ring is optionally substituted by halogen;
(c) $R^5$ is hydrogen or lower alkyl;
(d) $R^6$ is hydrogen or lower alkyl,
(e) $R^7$ is lower alkyl;
(f) $R^8$ is selected from the group consisting of:
  (1) lower alkyl,
  (2) lower halogenalkyl,
  (3) lower cycloalkylalkyl,
  (4) lower phenylalkyl, wherein the phenyl is optionally substituted by a substituent selected from the group consisting of lower alkyl, lower alkoxy and halogen,
  (5) lower heteroarylalkyl,
  (6) lower alkoxyalkyl, and
  (7) lower hydroxyalkyl.

2. A compound of claim 1 wherein one of $R^3$ and $R^4$ is selected from the group consisting of:
  (1) lower alkylamino,
  (2) lower dialkylamino,
  (3) cycloalkylamino, and
  (4) a heterocyclic ring selected from the group consisting of azetidinyl, pyrrolidinyl, piperidinyl, morpholinyl, thiomorpholinyl and azepanyl, said heterocyclic ring being optionally substituted by halogen;
and the other one of $R^3$ and $R^4$ is —$OR^8$.

3. A compound of claim 1, wherein $R^1$ is selected from the group consisting of lower alkyl, lower hydroxyalkyl, lower heterocyclylalkyl, —$CR^5R^6$—$COOR^7$ and —$CR^5R^6$—$CONH_2$.

4. A compound of claim 1, wherein $R^1$ is selected from the group consisting of lower alkyl, lower hydroxyalkyl, lower heterocyclylalkyl, and —$CR^5R^6$—$COOR^7$.

5. A compound of claim 1, wherein $R^1$ is lower hydroxyalkyl or —$CR^5R^6$—$COOR^7$.

6. A compound of claim 1, wherein $R^1$ is lower hydroxyalkyl.

7. A compound of claim 1, wherein $R^1$ is —$CR^5R^6$—$COOR^7$; and $R^5$ and $R^6$ independently from each other are lower alkyl.

8. A compound of claim 1, wherein:
(a) $R^4$ is selected from the group consisting of:
  (1) lower alkylamino,
  (2) lower dialkylamino, and
  (3) a heterocyclic ring selected from the group consisting of azetidinyl, pyrrolidinyl, piperidinyl, morpholinyl, thiomorpholinyl and azepanyl, said heterocyclic ring being optionally substituted by halogen; and
(b) $R^3$ is —$OR^8$.

9. A compound of claim 1, wherein:
(a) $R^3$ is selected from the group consisting of:
  (1) lower alkylamino; and
  (2) a heterocyclic ring selected from the group consisting of azetidinyl, pyrrolidinyl, piperidinyl, morpholinyl, thiomorpholinyl and azepanyl, said heterocyclic ring being optionally substituted by halogen; and
(b) $R^4$ is —$OR^8$.

10. A compound of claim 1, wherein one of $R^3$ and $R^4$ is a heterocyclic ring selected from the group consisting of azetidinyl, pyrrolidinyl, piperidinyl, morpholinyl, thiomorpholinyl and azepanyl, wherein said heterocyclic ring is optionally substituted by halogen.

11. A compound of claim 1, wherein $R^8$ is selected from the group consisting of:
  (1) lower alkyl,
  (2) lower halogenalkyl,
  (3) lower cycloalkylalkyl,
  (4) lower phenylalkyl, wherein the phenyl is optionally substituted by a substituent selected from the group consisting of lower alkyl, lower alkoxy and halogen, and
  (5) lower alkoxyalkyl.

12. A compound of claim 1, wherein $R^8$ is selected from the group consisting of:
  (1) lower cycloalkylalkyl,
  (2) lower phenylalkyl, wherein the phenyl is optionally substituted by a group selected from the group consisting of lower alkyl, lower alkoxy and halogen, and
  (3) lower heteroarylalkyl, wherein said heteroaryl is pyridyl or pyrimidinyl.

13. A compound of claim 1, wherein $R^8$ is lower halogenalkyl or lower alkoxyalkyl.

14. A compound of claim 1, selected from the group consisting of:
  6-cyclobutylmethoxy-5-pyrrolidin-1-yl-pyrazine-2-carboxylic acid (3-methyl-butyl)-amide,
  6-cyclopropylmethoxy-5-pyrrolidin-1-yl-pyrazine-2-carboxylic acid cyclohexylamide,
  6-cyclopropylmethoxy-5-pyrrolidin-1-yl-pyrazine-2-carboxylic acid ((S)-1-hydroxymethyl-3-methyl-butyl)-amide,
  6-cyclopentyl methoxy-5-pyrrolidin-1-yl-pyrazine-2-carboxylic acid (3-methyl-butyl)-amide,
  6-cyclopentyl methoxy-5-pyrrolidin-1-yl-pyrazine-2-carboxylic acid (tetrahydro-pyran-4-ylmethyl)-amide,
  6-cyclopentylmethoxy-5-pyrrolidin-1-yl-pyrazine-2-carboxylic acid ((1R,2R)-2-hydroxy-cyclohexyl)-amide,
  6-benzyloxy-5-pyrrolidin-1-yl-pyrazine-2-carboxylic acid ((S)-1-hydroxymethyl-3-methyl-butyl)-amide,
  6-cyclopropylmethoxy-5-piperidin-1-yl-pyrazine-2-carboxylic acid ((S)-1-hydroxymethyl-3-methyl-butyl)-amide, and
  6-propoxy-5-pyrrolidin-1-yl-pyrazine-2-carboxylic acid ((S)-1-hydroxymethyl-3-methyl-butyl)-amide,
or a pharmaceutically acceptable salt thereof.

15. A compound of claim 1, selected from the group consisting of:
- 6-butoxy-5-pyrrolidin-1-yl-pyrazine-2-carboxylic acid ((S)-1-hydroxymethyl-3-methyl-butyl)-amide,
- 6-(4-fluoro-benzyloxy)-5-pyrrolidin-1-yl-pyrazine-2-carboxylic acid ((S)-1-hydroxymethyl-3-methyl-butyl)-amide,
- 6-(2-methoxy-ethoxy)-5-pyrrolidin-1-yl-pyrazine-2-carboxylic acid ((S)-1-hydroxymethyl-3-methyl-butyl)-amide,
- 2-ethyl-2-{[5-pyrrolidin-1-yl-6-(2,2,2-trifluoro-ethoxy)-pyrazine-2-carbonyl]-amino}-pentanoic acid methyl ester,
- (S)-2-[(6-cyclobutylmethoxy-5-pyrrolidin-1-yl-pyrazine-2-carbonyl)-amino]-propionic acid methyl ester,
- (R)-2-[(6-cyclobutylmethoxy-5-pyrrolidin-1-yl-pyrazine-2-carbonyl)-amino]-propionic acid methyl ester,
- 6-cyclobutylmethoxy-5-pyrrolidin-1-yl-pyrazine-2-carboxylic acid ((S)-1-hydroxymethyl-3-methyl-butyl)-amide,
- (S)-2-[(6-cyclopentylmethoxy-5-pyrrolidin-1-yl-pyrazine-2-carbonyl)-amino]-propionic acid methyl ester,
- (R)-2-[(6-cyclopentylmethoxy-5-pyrrolidin-1-yl-pyrazine-2-carbonyl)-amino]-propionic acid methyl ester, and
- (S)-4-methyl-2-{[6-(pyridin-2-ylmethoxy)-5-pyrrolidin-1-yl-pyrazine-2-carbonyl]-amino}-pentanoic acid methyl ester, or a pharmaceutically acceptable salt thereof.

16. A compound of claim 1, selected from the group consisting of:
- (S)-4-methyl-2-{[6-(pyrimidin-2-ylmethoxy)-5-pyrrolidin-1-yl-pyrazine-2-carbonyl]-amino}-pentanoic acid methyl ester,
- 2-ethyl-2-[(6-isopropoxy-5-piperidin-1-yl-pyrazine-2-carbonyl)-amino]-butyric acid methyl ester,
- 6-(2,2-dimethyl-propoxy)-5-piperidin-1-yl-pyrazine-2-carboxylic acid ((S)-1-hydroxymethyl-3-methyl-butyl)-amide,
- 6-(2-methoxy-ethoxy)-5-piperidin-1-yl-pyrazine-2-carboxylic acid ((S)-1-hydroxymethyl-3-methyl-butyl)-amide,
- (S)-2-{[6-(2-methoxy-ethoxy)-5-piperidin-1-yl-pyrazine-2-carbonyl]-amino}-4-methyl-pentanoic acid methyl ester,
- 2-ethyl-2-{[5-morpholin-4-yl-6-(2,2,2-trifluoro-ethoxy)-pyrazine-2-carbonyl]-amino}-butyric acid methyl ester,
- (S)-4-methyl-2-{[5-morpholin-4-yl-6-(2,2,2-trifluoro-ethoxy)-pyrazine-2-carbonyl]-amino}-pentanoic acid methyl ester,
- 6-(2,2-dimethyl-propoxy)-5-morpholin-4-yl-pyrazine-2-carboxylic acid ((S)-1-hydroxymethyl-3-methyl-butyl)-amide,
- 2-ethyl-2-{[6-(2-methoxy-ethoxy)-5-morpholin-4-yl-pyrazine-2-carbonyl]-amino}-butyric acid methyl ester, and
- 2-{[5-cyclohexylamino-6-(2,2,2-trifluoro-ethoxy)-pyrazine-2-carbonyl]-amino}-2-ethyl-butyric acid methyl ester, or a pharmaceutically acceptable salt thereof.

17. A compound of claim 1, selected from the group consisting of:
- 2-{[5-cyclohexylamino-6-(2,2-dimethyl-propoxy)-pyrazine-2-carbonyl]-amino}-2-ethyl-butyric acid methyl ester,
- 2-{[5-cyclohexylamino-6-(2-methoxy-ethoxy)-pyrazine-2-carbonyl]-amino}-2-ethyl-butyric acid methyl ester,
- 2-{[5-butylamino-6-(2,2,2-trifluoro-ethoxy)-pyrazine-2-carbonyl]-amino}-2-ethyl-butyric acid methyl ester,
- 2-{[5-butylamino-6-(2-methoxy-ethoxy)-pyrazine-2-carbonyl]-amino}-2-ethyl-butyric acid methyl ester,
- 2-[(5-diethylamino-6-isopropoxy-pyrazine-2-carbonyl)-amino]-2-ethyl-butyric acid methyl ester,
- 5-diethylamino-6-(2-methoxy-ethoxy)-pyrazine-2-carboxylic acid ((S)-1-hydroxymethyl-3-methyl-butyl)-amide,
- (S)-2-{[5-diethylamino-6-(2-methoxy-ethoxy)-pyrazine-2-carbonyl]-amino}-4-methyl-pentanoic acid methyl ester,
- 5-diethylamino-6-(2-methoxy-ethoxy)-pyrazine-2-carboxylic acid ((S)-1-carbamoyl-3-methyl-butyl)-amide,
- 2-{[5-(4,4-difluoro-piperidin-1-yl)-6-(2,2-dimethyl-propoxy)-pyrazine-2-carbonyl]-amino}-2-ethyl-butyric acid methyl ester,
- 6-cyclopentylmethoxy-5-(4,4-difluoro-piperidin-1-yl)-pyrazine-2-carboxylic acid ((S)-1-hydroxymethyl-3-methyl-butyl)-amide, and
- (S)-2-{[6-cyclopentylmethoxy-5-(4,4-difluoro-piperidin-1-yl)-pyrazine-2-carbonyl]-amino}-4-methyl-pentanoic acid methyl ester, or a pharmaceutically acceptable salt thereof.

18. A compound of claim 1, selected from the group consisting of:
- 2-{[5-(4,4-difluoro-piperidin-1-yl)-6-(2-methoxy-ethoxy)-pyrazine-2-carbonyl]-amino}-2-ethyl-butyric acid methyl ester,
- 2-ethyl-2-{[6-piperidin-1-yl-5-(2,2,2-trifluoro-ethoxy)-pyrazine-2-carbonyl]-amino}-butyric acid methyl ester, and
- 5-cyclopropylmethoxy-6-piperidin-1-yl-pyrazine-2-carboxylic acid ((S)-1-hydroxymethyl-3-methyl-butyl)-amide, or a pharmaceutically acceptable salt thereof.

19. A compound of claim 1, selected from the group consisting of:
- 6-cyclopropylmethoxy-5-pyrrolidin-1-yl-pyrazine-2-carboxylic acid ((S)-1-hydroxymethyl-3-methyl-butyl)-amide,
- 6-cyclopropylmethoxy-5-piperidin-1-yl-pyrazine-2-carboxylic acid ((S)-1-hydroxymethyl-3-methyl-butyl)-amide,
- 6-(4-fluoro-benzyloxy)-5-pyrrolidin-1-yl-pyrazine-2-carboxylic acid ((S)-1-hydroxymethyl-3-methyl-butyl)-amide,
- 2-ethyl-2-{[5-pyrrolidin-1-yl-6-(2,2,2-trifluoro-ethoxy)-pyrazine-2-carbonyl]-amino}-pentanoic acid methyl ester,
- 6-cyclobutylmethoxy-5-pyrrolidin-1-yl-pyrazine-2-carboxylic acid ((S)-1-hydroxymethyl-3-methyl-butyl)-amide, and
- (R)-2-[(6-cyclopentylmethoxy-5-pyrrolidin-1-yl-pyrazine-2-carbonyl)-amino]-propionic acid methyl ester, or a pharmaceutically acceptable salt thereof.

20. A pharmaceutical composition comprising a therapeutically effective amount of a compound of claim 1 and a pharmaceutically acceptable carrier.

21. A compound selected from the group consisting of:
- 6-[(2-methoxy-ethyl)-methyl-amino]-5-piperidin-1-yl-pyrazine-2-carboxylic acid ((S)-1-hydroxymethyl-3-methyl-butyl)-amide,
- 2-{[6-(4-fluoro-phenyl)-5-piperidin-1-yl-pyrazine-2-carbonyl]-amino}-2-methyl-propionic acid methyl ester, and 2-{[6-(4-chloro-phenyl)-5-pyrrolidin-1-yl-pyrazine-2-carbonyl]-amino}-2-methyl-propionic acid methyl ester, or a pharmaceutically acceptable salt thereof.

22. A compound selected from the group consisting of:

(R)-2-{[6-(4-chloro-phenyl)-5-(2,2,2-trifluoro-ethoxy)-pyrazine-2-carbonyl]-amino}-3-methyl-butyric acid methyl ester, (R)-2-{[6-(3-chloro-phenyl)-5-(2,2,2-trifluoro-ethoxy)-pyrazine-2-carbonyl]-amino}-3-methyl-butyric acid methyl ester, (R)-2-{[6-(3-chloro-phenyl)-5-cyclopropyl methoxy-pyrazine-2-carbonyl]-amino}-3-methyl-butyric acid methyl ester, 2-{[5-cyclopropyl methoxy-6-(4-fluoro-phenyl)-pyrazine-2-carbonyl]-amino}-2-methyl-propionic acid methyl ester, and 2-{[6-(4-chloro-phenyl)-5-cyclopropyl methoxy-pyrazine-2-carbonyl]-amino}-2-methyl-propionic acid methyl ester, or a pharmaceutically acceptable salt thereof.

* * * * *